US011872554B2

(12) United States Patent
Schenk zu Schweinsberg et al.

(10) Patent No.: US 11,872,554 B2
(45) Date of Patent: Jan. 16, 2024

(54) MICROFLUIDIC DEVICES AND RELATED METHODS

(71) Applicant: ABBOTT DIAGNOSTICS SCARBOROUGH, INC., Scarborough, ME (US)

(72) Inventors: Alexander Schenk zu Schweinsberg, Jena (DE); Austin Matthew Derfus, Solana Beach, CA (US); Justin Davidson, San Diego, CA (US); Karthikeyan Kumaravadivelu, San Diego, CA (US); Maulik Vinod Patel, La Crescenta, CA (US); Olaf Piepenburg, Saffron Walden (GB); Catherine Jean Greenwood, Sawbridgeworth (GB); Oliver Nentwich, Cambridge (GB)

(73) Assignee: ABBOTT DIAGNOSTICS SCARBOROUGH, INC., Scarborough, ME (US)

( * ) Notice: Subject to any disclaimer, the term of this patent is extended or adjusted under 35 U.S.C. 154(b) by 0 days.

(21) Appl. No.: 16/812,961

(22) Filed: Mar. 9, 2020

(65) Prior Publication Data

US 2020/0391209 A1 Dec. 17, 2020

Related U.S. Application Data

(62) Division of application No. 15/906,899, filed on Feb. 27, 2018, now Pat. No. 10,632,464.
(Continued)

(51) Int. Cl.
*G01N 1/00* (2006.01)
*B01L 3/00* (2006.01)
(Continued)

(52) U.S. Cl.
CPC ....... *B01L 3/502715* (2013.01); *B01L 3/5029* (2013.01); *G01N 1/14* (2013.01);
(Continued)

(58) Field of Classification Search
CPC .................. C12Q 1/6844; B01L 3/502715
See application file for complete search history.

(56) References Cited

U.S. PATENT DOCUMENTS 6,300,138 B1   10/2001   Gleason et al.
6,645,758 B1   11/2003   Schnipelsky et al.
(Continued)

FOREIGN PATENT DOCUMENTS

WO   WO2010141940   12/2010
WO   WO2017147486   8/2017
WO   WO2017152122   9/2017

OTHER PUBLICATIONS

Van Elden, Simultaneous Detection of Influenza Viruses A and B Using Real-Time Quantitative PCR, J Clin Immun, 39(1): 196-200, 2001.*
(Continued)

*Primary Examiner* — Nathan A Bowers
(74) *Attorney, Agent, or Firm* — Casimir Jones, S.C.; Thomas A. Isenbarger

(57) ABSTRACT

A microfluidic device includes an inlet port configured to receive a sample, a first reaction chamber fluidically coupled to the inlet port, a first pump fluidically coupled to the inlet port, a second pump fluidically coupled to a mixing chamber, a metering channel fluidically coupled to the first reaction chamber and to the mixing chamber, and one or more second reaction chambers fluidically coupled to the mixing chamber. The first pump is configured to move fluid from the inlet port to the first reaction chamber and from the first pump to the inlet port. The second pump is configured
(Continued)

to move fluid from the second pump to the mixing chamber, from the first reaction chamber to the mixing chamber, and from the mixing chamber to the one or more second reaction chambers.

18 Claims, 24 Drawing Sheets

Related U.S. Application Data

(60) Provisional application No. 62/464,576, filed on Feb. 28, 2017.

(51) Int. Cl.
*G01N 1/14* (2006.01)
*G01N 35/00* (2006.01)
*G01N 1/02* (2006.01)
*G01N 1/38* (2006.01)
*G01N 35/10* (2006.01)

(52) U.S. Cl.
CPC .. *G01N 35/00069* (2013.01); *B01L 2200/027* (2013.01); *B01L 2200/082* (2013.01); *B01L 2300/0816* (2013.01); *B01L 2300/0864* (2013.01); *B01L 2300/0867* (2013.01); *B01L 2400/0478* (2013.01); *B01L 2400/0655* (2013.01); *G01N 1/38* (2013.01); *G01N 2001/028* (2013.01); *G01N 2035/00158* (2013.01); *G01N 2035/1034* (2013.01)

(56) References Cited

U.S. PATENT DOCUMENTS

| | | | | |
|---|---|---|---|---|
| 7,270,981 | B2 | 9/2007 | Armes | |
| 7,399,590 | B2 * | 7/2008 | Piepenburg | .......... C12Q 1/6844 435/6.14 |
| 7,435,561 | B2 | 10/2008 | Piepenburg et al. | |
| 7,666,598 | B2 | 2/2010 | Piepenburg et al. | |
| 8,062,850 | B2 | 11/2011 | Piepenburg et al. | |
| 8,071,308 | B2 | 12/2011 | Piepenburg et al. | |
| 8,394,608 | B2 | 3/2013 | Ririe et al. | |
| 8,580,507 | B2 | 11/2013 | Piepenburg et al. | |
| 8,637,253 | B2 | 1/2014 | Piepenburg et al. | |
| 9,057,097 | B2 | 6/2015 | Piepenburg | |
| 9,469,867 | B2 | 10/2016 | Piepenburg | |
| 9,562,263 | B2 | 2/2017 | Maples et al. | |
| 9,562,264 | B2 | 2/2017 | Maples et al. | |
| 2004/0265172 | A1 | 12/2004 | Pugia et al. | |
| 2006/0166357 | A1 | 7/2006 | Takayama et al. | |
| 2009/0017453 | A1 | 1/2009 | Maples et al. | |
| 2009/0029421 | A1 | 1/2009 | Piepenburg et al. | |
| 2009/0081670 | A1 | 3/2009 | Maples et al. | |
| 2009/0111089 | A1 | 4/2009 | Lindstrom et al. | |
| 2010/0105029 | A1 | 4/2010 | Ririe et al. | |
| 2010/0311127 | A1 * | 12/2010 | Piepenburg | .......... C12Q 1/6844 435/91.5 |
| 2011/0053153 | A1 * | 3/2011 | Piepenburg | ............ C07H 21/00 435/5 |
| 2012/0244534 | A1 * | 9/2012 | Ching | ..................... B01L 3/502 435/6.11 |
| 2015/0050172 | A1 | 2/2015 | Haupt | |
| 2015/0258544 | A1 | 9/2015 | Stern et al. | |
| 2016/0175835 | A1 | 6/2016 | Taylor et al. | |
| 2021/0363575 | A1 * | 11/2021 | Nobile | ..................... B01L 7/52 |

OTHER PUBLICATIONS

International Search Report of related PCT/US2018/019975, dated Jun. 1, 2018, 22 pages.
International Search Report of related PCT/US2017/020782, dated Sep. 8, 2017, 15 pages.
Lin et al., Origins and evolution of the recA RAD51 gene family: Evidence for ancient gene duplication and endosymbiotic gene transfer, PNAS USA 103:10328-10333, 2006, 6 pages.
Hocek, Nucleobase modification as redox DNA labelling for electrochemical detection, Chem. Soc. Rev., 2011, 40, 5802-5814, 14 pages.
Search Report of European Application No. 18761718.8 dated Nov. 24, 2020 (13 pages).
Search Report of European Application No. 18761718.8 dated Feb. 25, 2021 (12 pages).

* cited by examiner

0s 1.5s 2.5s

7s

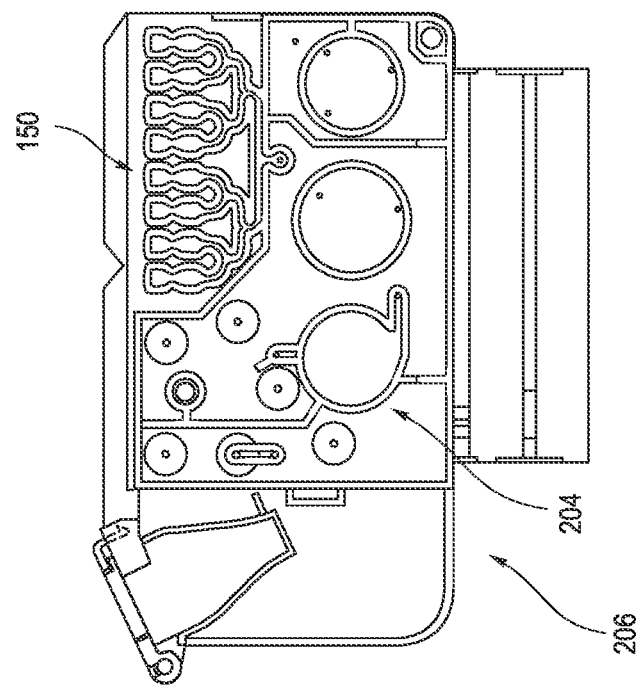
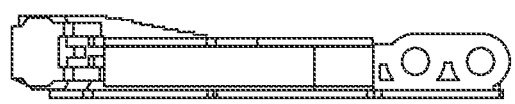
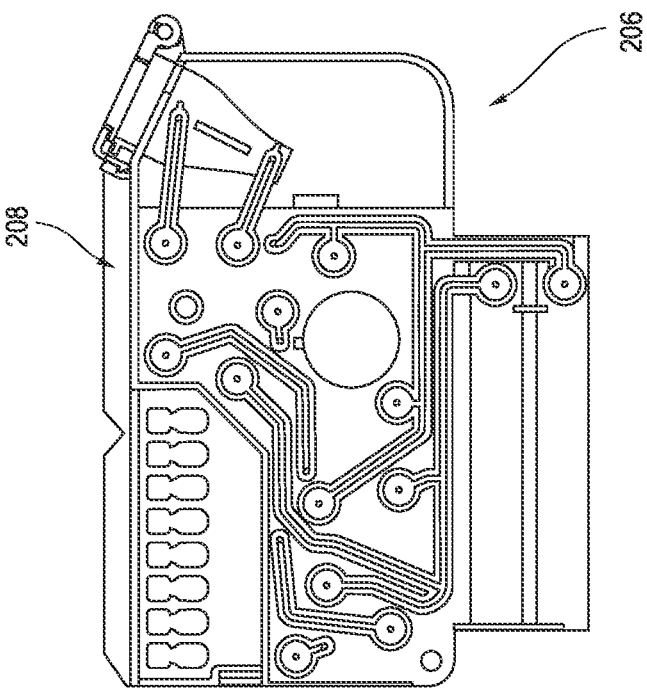
Fig. 24C
Fig. 24B
Fig. 24A

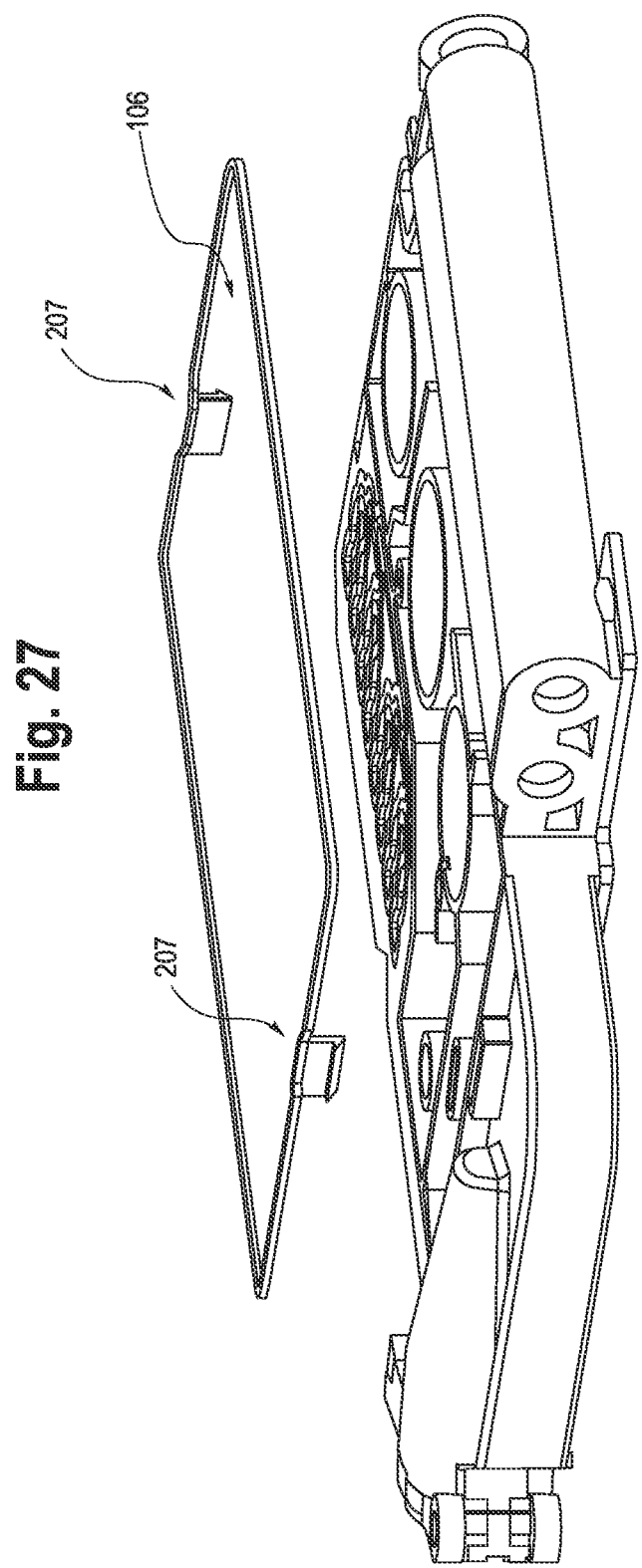

MICROFLUIDIC DEVICES AND RELATED METHODS

CROSS-REFERENCE TO RELATED APPLICATION

This application claims the benefit of U.S. Patent Application Ser. No. 62/464,576 entitled "MICROFLUIDIC DEVICES AND RELATED METHODS" filed Feb. 28, 2017, which is hereby incorporated by reference in its entirety.

STATEMENT OF GOVERNMENT INTEREST

This invention was made with government support under HHSO100201400011C awarded by the U.S. Department of Health and Human Services. The government has certain rights in the invention.

TECHNICAL FIELD

This disclosure relates to microfluidic devices, and more particularly to microfluidic devices used to perform diagnostic assays.

BACKGROUND

Microfluidic devices are designed to precisely control fluid flows within geometrically constrained networks for a number of applications. In some examples, microfluidic devices may be employed to perform certain molecular diagnostic assays, such as those based on isothermal nucleic acid amplification methods (e.g., Recombinase Polymerase Amplification (RPA) or Nicking and Extension Amplification Reaction (NEAR)) to detect trace levels of nucleic acids. In some instances, microfluidic devices can facilitate point-of-care (POC) testing and can increase accessibility and speed of a diagnostic assay, such as an assay that can detect influenza (Flu) and Respiratory Syncytial Virus (RSV). For example, microfluidic devices may facilitate rapid detection of target nucleic acids present in Flu and/or RSV viruses.

SUMMARY

Microfluidic devices disclosed herein are designed for performing diagnostic assays (e.g., an assay that can detect influenza (Flu) and Respiratory Syncytial Virus (RSV)) in which one or more target nucleic acids can be detected. For example, a microfluidic device includes a cartridge assembly, a elastomer layer, and a lid. The cartridge assembly and the elastomer layer together provide a series of fluidly coupled ports, channels, chambers, reservoirs, valves, and accessory components by which the assay can be carried out to detect the presence of the one or more target nucleic acids in a sample provided to the microfluidic device. The lid covers the cartridge assembly and provides a layer through which the one or more target nucleic acids can be detected within the cartridge assembly.

The cartridge assembly includes a cartridge, a cap, a seal, plugs, magnets, first and second reaction pellets. The cartridge defines a geometry of a microfluidic network and a sample chamber that provides an inlet port to the microfluidic network. The sample chamber is sized and shaped to accommodate sample collection devices (e.g., swabs) and includes a relatively wide first portion and a relatively narrow second portion, such that a tip of a swab within the sample chamber is completely wetted when a liquid reagent is delivered to the sample chamber.

The cartridge also defines two on-board pumps that are operable to force fluid into the microfluidic network or to withdraw fluid from the microfluidic network. The cartridge defines a first reaction chamber that is primed with the first reaction pellet, a mixing chamber, and multiple second reaction chambers that are primed with respective second reaction pellets such that multiplexing can be carried out within the microfluidic device. Mixing in the second reaction chambers may occur via one or both of mixing and acoustic microstreaming. Each of the second reaction chambers includes an identical air spring that permits an even distribution of fluid within the second reaction chambers such that a filling level among the second reaction chambers automatically equilibrates as a result of backpressure that is generated as the second reaction chambers fill with fluid. Accordingly, the second reaction chambers can fill with precise, accurate, equivalent volumes of fluid and achieve an equivalent pressure.

Additionally, a volume formed between the cartridge and the lid and external to the microfluidic network provides a waste reservoir (e.g., an air reservoir) that buffers an air pressure in the microfluidic network, such that the microfluidic device does not need to include a separate pressure equilibration mechanism. Cavities within the cartridge and corresponding regions of the elastomer layer lying along the cavities can cooperate to form valves at selected locations along the microfluidic network to control fluid flows. The microfluidic device is configured to provide a closed system such that a risk of leakage contamination to an ambient environment is significantly reduced as compared to conventional devices used to carry out similar assays. Owing at least in part to a configuration of the microfluidic device, the microfluidic device can be used to carry out a Flu/RSV assay in less than about 15 min.

For example, in some embodiments, provided herein is a microfluidic device comprising: an inlet port configured to receive a sample; a first reaction chamber fluidically coupled to the inlet port; a first pump fluidically coupled to the inlet port; a second pump fluidically coupled to a mixing chamber; a metering channel fluidically coupled to the first reaction chamber and to the mixing chamber; and one or more second reaction chambers fluidically coupled to the mixing chamber; wherein the first pump is configured to move fluid from the inlet port to the first reaction chamber and from the first pump to the inlet port; and wherein the second pump is configured to move fluid from the second pump to the mixing chamber, from the first reaction chamber to the mixing chamber, and from the mixing chamber to the one or more second reaction chambers. In some embodiments, the microfluidic device further comprises a waste reservoir configured to modulate a fluid pressure within the microfluidic device. In some embodiments, the first reaction chamber comprises a first set of amplification reagents (e.g., Recombinase Polymerase Amplification (RPA) reagents). In some embodiments, the RPA reagents are freeze dried. In some embodiments, the first reaction chamber further comprises a catalytic reagent (e.g., magnesium). In some embodiments, the first set of amplification reagents comprises oligomers. In some embodiments, the mixing chamber comprises a second set of amplification reagents (e.g., RPA reagents). In some embodiments, the RPA reagents are freeze dried. In some embodiments, the one or more second reaction chambers each comprise a second set of amplification reagents (e.g., RPA reagents). In some embodiments, the RPA reagents are freeze dried. In some embodiments, the second set of amplification reagents comprises oligomers. In some embodiments, the first pump comprises a first buffer. In some embodiments, the first pump comprises a first buffer and a lysing agent. In some embodiments, the second pump comprises a second buffer. In some embodiments, the second pump comprises a second buffer and a lysing agent. In some embodiments, the first pump comprises a catalytic reagent. In some embodiments, the second pump comprises a catalytic reagent. In some embodiments, the catalytic reagent comprises magnesium. In some embodiments, each of the one or more second reaction chambers is a detection chamber. In some embodiments, a portion of each detection chamber is optically transparent. In some embodiments, the first reaction chamber is configured to be coupled to a heating unit. In some embodiments, the inlet port is configured to be coupled to a heating unit. In some embodiments, the first reaction chamber comprises a mixing means or is coupled to a mixing means. In some embodiments, the mixing chamber comprises a mixing means or is coupled to a mixing means. In some embodiments, the one or more second reaction chambers each comprises a mixing means or is coupled to a mixing means. In some embodiments, the mixing means is a magnet. In some embodiments, the mixing means is operated by acoustic streaming. In some embodiments, the inlet port comprises a sample, the first pump comprises a first buffer, and the first pump is configured to deliver the first buffer from the first pump to the inlet port to generate a diluted sample comprising the sample and the first buffer. In some embodiments, the first reaction chamber comprises a first set of amplification reagents, and the first pump is configured to provide a portion of the diluted sample from the inlet port to the first reaction chamber to generate a first reaction mixture comprising the diluted sample and the first set of amplification reagents. In some embodiments, the second pump is configured to provide a portion of the first reaction mixture from the first reaction chamber to the mixing chamber via the metering channel. In some embodiments, the second pump comprises a second buffer, the second pump is configured to deliver the second buffer from the second pump to the mixing chamber via the metering channel, and the second buffer combines with the portion of the first reaction mixture to generate a diluted first reaction mixture. In some embodiments, the one or more second reaction chambers each comprises a second set of amplification reagents, and the second pump is configured to deliver a portion of the diluted first reaction mixture from the mixing chamber to each of the one or more second reaction chambers to generate second reaction mixtures comprising the diluted first reaction mixture and the second set of amplification reagents. In some embodiments, the second set of amplification reagents comprises oligomers. In some embodiments, the mixing chamber comprises a second set of amplification reagents, the second reagent chamber comprises a second buffer, the second pump is configured to deliver the second buffer from the second reagent chamber to the mixing chamber via the metering channel, and the second buffer combines with the portion of the first reaction mixture and the second set of amplification reagents to generate a second reaction mixture. In some embodiments, the second pump is configured to deliver a portion of the second reaction mixture to each of the one or more second reaction chambers. In some embodiments, each of the one or more second reaction chambers comprises oligomers. In some embodiments, the microfluidic device comprises two, three, four, five, six, seven, or eight second reaction chambers. In some embodiments, the microfluidic device further comprises a series of valves. In some embodiments, the microfluidic device further comprises alignment holes for connection of the microfluidic device to a reader configured to process the sample and deliver the sample to the microfluidic device. In some embodiments, the connection ports are configured to lockably engage with the reader. In some embodiments, the microfluidic device is a disposable cartridge. In some embodiments, the first pump and the second pump are syringe pumps. In some embodiments, the inlet port comprises a cap. In some embodiments, the cap comprises a gasket comprising a gasket seal rib. In some embodiments, the cap comprises a detent feature to secure the cap in an open position.

Additional embodiments provide reader configured to receive a microfluidic device as described herein, the reader comprising a detector configured to detect the presence of second reaction products in the one or more second reaction chambers. In some embodiments, the microfluidic device or the reader comprises a cap position detection component configured to detect cap closure or cap leaks. In some embodiments, the cap position detection component comprises one or more components (e.g., an optical cap closure sensor and/or a pressure sensor). In some embodiments, the optical cap closure sensor comprises an optical beam that is broken when the cap is in a closed, sealed position. In some embodiments, the pressure sensor assesses the ability of the cap to resist pressure. In some embodiments, pressure is generated using a pump of the device. In some embodiments, a pressure outside of a predetermined range is indicative of a cap that is not sealed. In some embodiments, the reader is configured to halt operation of the reader or the microfluidic device when the cap is not identified as sealed.

Yet other embodiments provide a method comprising: providing a sample fluid comprising a target nucleic acid to a microfluidic device, the target nucleic acid comprising at least one target polynucleotide sequence; and amplifying the at least one target polynucleotide sequence under isothermal conditions, wherein the amplifying comprises: performing a first round of amplification on the target polynucleotide sequence to yield a first amplification product comprising a first amplified polynucleotide sequence; and performing a second round of amplification on the first amplified polynucleotide sequence to yield a second amplification product comprising a second amplified polynucleotide sequence, wherein the second amplified polynucleotide sequence comprises a smaller sequence completely contained within the first amplified polynucleotide sequence produced during the first round of amplification. In some embodiments, the method further comprises detecting the second amplification product. In some embodiments, detection of the second amplification product comprises: labeling the second amplification product with a first oligonucleotide linked to a fluorophore and a quencher to yield a labeled second product; cleaving the quencher from the labeled second amplification product; and optically detecting a signal from the fluorophore, wherein a detectable signal is indicative of the presence of the second amplification product. In some embodiments, cleaving the quencher is performed using a nuclease. In some embodiments, the nuclease targets double-stranded DNA. In some embodiments, the nuclease is formamidopyrimine-DNA glycosylase. In some embodiments, the step of amplifying comprises performing a first round of amplification, wherein the amplification is RPA. In some embodiments, the step of amplifying comprises performing a second round of amplification, wherein the amplification is RPA. In some embodiments, the step of amplifying comprises performing a first round of amplification, wherein the amplification is RPA, and a second round of amplification, wherein the amplification is RPA. In some embodiments, the sample is blood, sputum, mucus, saliva, tears, or urine. In some embodiments, the method further comprises the step of obtaining the sample from an animal. In some embodiments, the sample is obtained from an animal and the animal is a human. In some embodiments, the target nucleic acid is a target nucleic acid of an animal pathogen. In some embodiments, the animal pathogen is a single-stranded DNA virus, double-stranded DNA virus, or single-stranded RNA virus. In some embodiments, the animal pathogen is a bacterium. In some embodiments, the target nucleic acid is double-stranded DNA, single-stranded DNA, or RNA. In some embodiments, the target nucleic acid is selected from, for example, genomic DNA, plasmid DNA, viral DNA, mitochondrial DNA, cDNA, synthetic double-stranded DNA or synthetic single-stranded DNA. In some embodiments, the target nucleic acid is viral DNA or viral RNA. In some embodiments, the animal pathogen is an influenza A virus, an influenza B virus, or Respiratory Syncytial Virus (RSV). In some embodiments, the target nucleic acid comprises two target polynucleotide sequences. In some embodiments, the target nucleic acid comprises three target polynucleotide sequences. In some embodiments, the method further comprises the step of mixing the sample with RPA reagents prior to the step of providing the sample to the microfluidic device. In some embodiments, the second amplification products are detected in less than about 30 minutes, in less than about 15 minutes, in less than about 10 minutes, or in less than about five minutes after the step of providing the sample to the microfluidic device. In some embodiments, the second amplification products are detected in real time. In some embodiments, the method further comprises the step of lysing the sample prior to amplification. In some embodiments, the step of lysing comprises combining the sample with a lysing agent. In some embodiments, the lysing agent is an enzyme. In some embodiments, the step of lysing comprises a mechanical means. In some embodiments, the step of lysing comprises heating the sample.

Still further embodiments provide a method comprising: providing a sample comprising a target nucleic acid to a microfluidic device, the target nucleic acid comprising at least one target polynucleotide sequence; and amplifying the at least one target polynucleotide sequence, wherein the amplifying comprises: performing a first round of amplification on the target polynucleotide sequence to yield a first amplification product comprising a first amplified polynucleotide sequence; performing one or more additional successive rounds of amplification on the first amplified polynucleotide sequence to form additional amplification products, wherein the amplification product from each successive n+1 round of amplification comprises an amplified polynucleotide sequence that is a smaller sequence completely contained within the amplified polynucleotide sequence produced during the previous nth round; performing a final round of amplification on the penultimate amplified polynucleotide sequence to yield a final amplification product; and detecting the final amplification product.

Other features and advantages will be apparent from the following detailed description, figures, and claims.

DESCRIPTION OF DRAWINGS

This patent or patent application publication contains at least one drawing executed in color. Copies of this patent or patent application publication with color drawing(s) will be provided by the USPTO upon request and payment of an associated fee.

FIG. 24 shows an exemplary microfluidic device.

FIG. 27 shows exemplary lid design embodiments.

DETAILED DESCRIPTION

Figure 1:
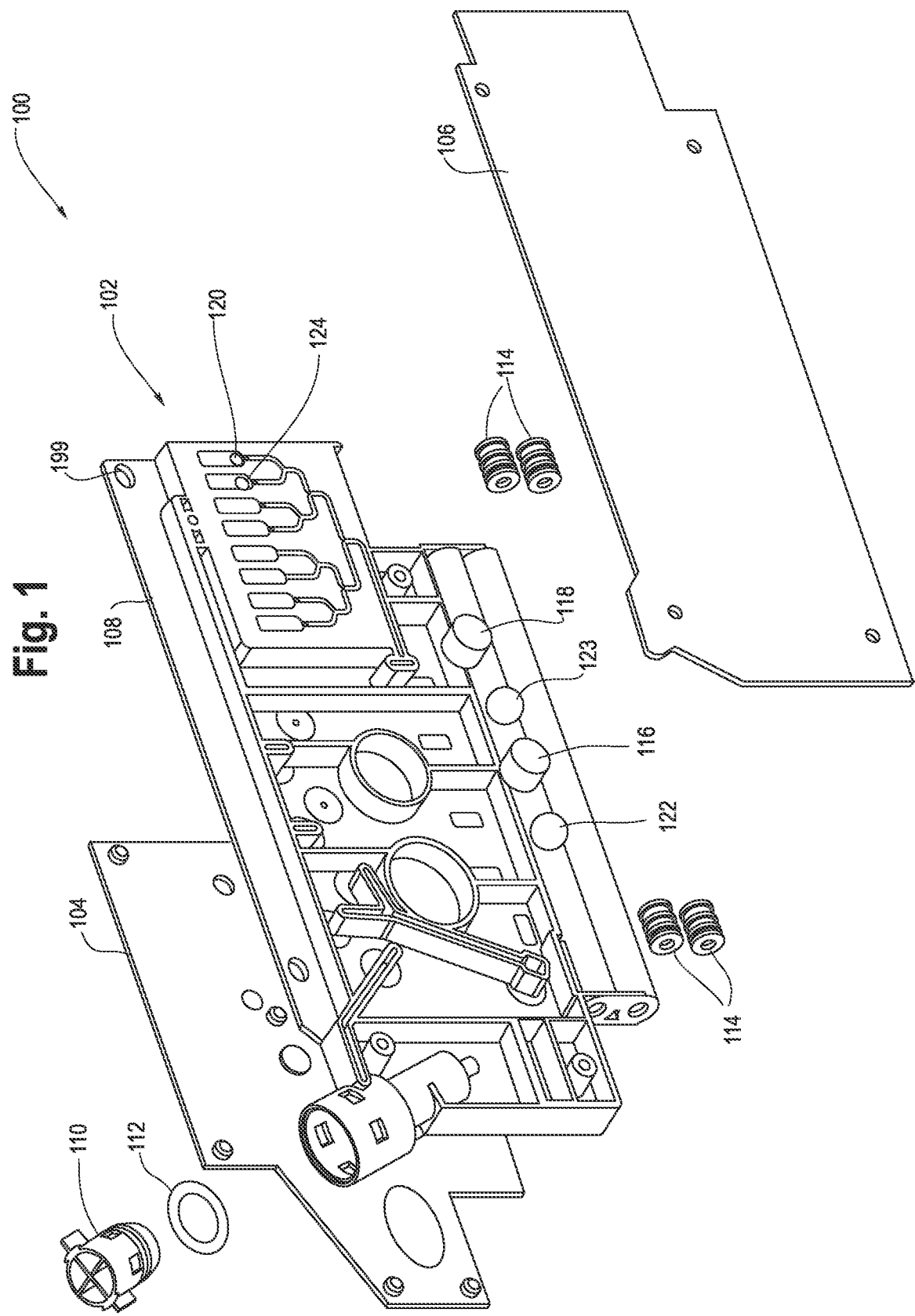
FIG. 1 illustrates an exploded of view of a microfluidic device used to perform an assay.
Figure 2:
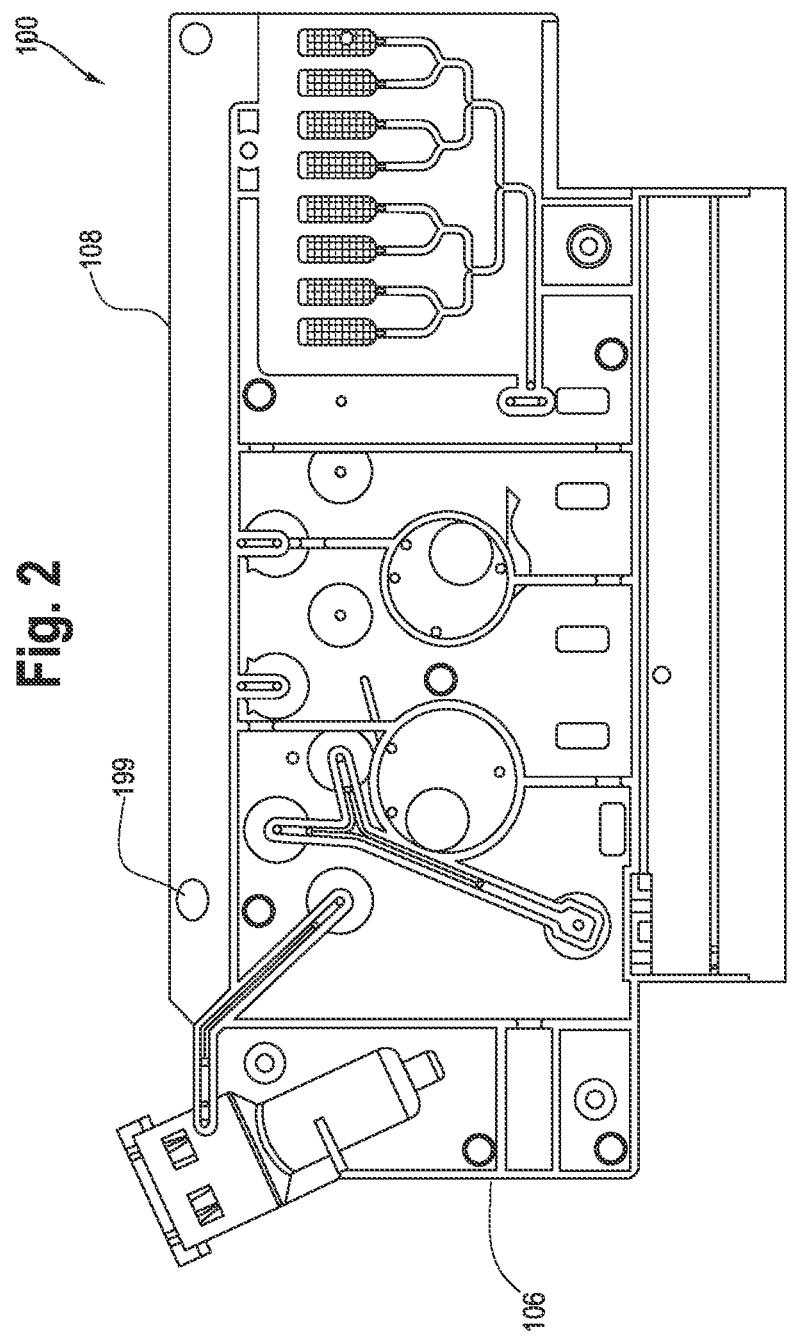
FIG. 2 illustrates a frontal view of the microfluidic device of FIG. 1.
Figure 3:
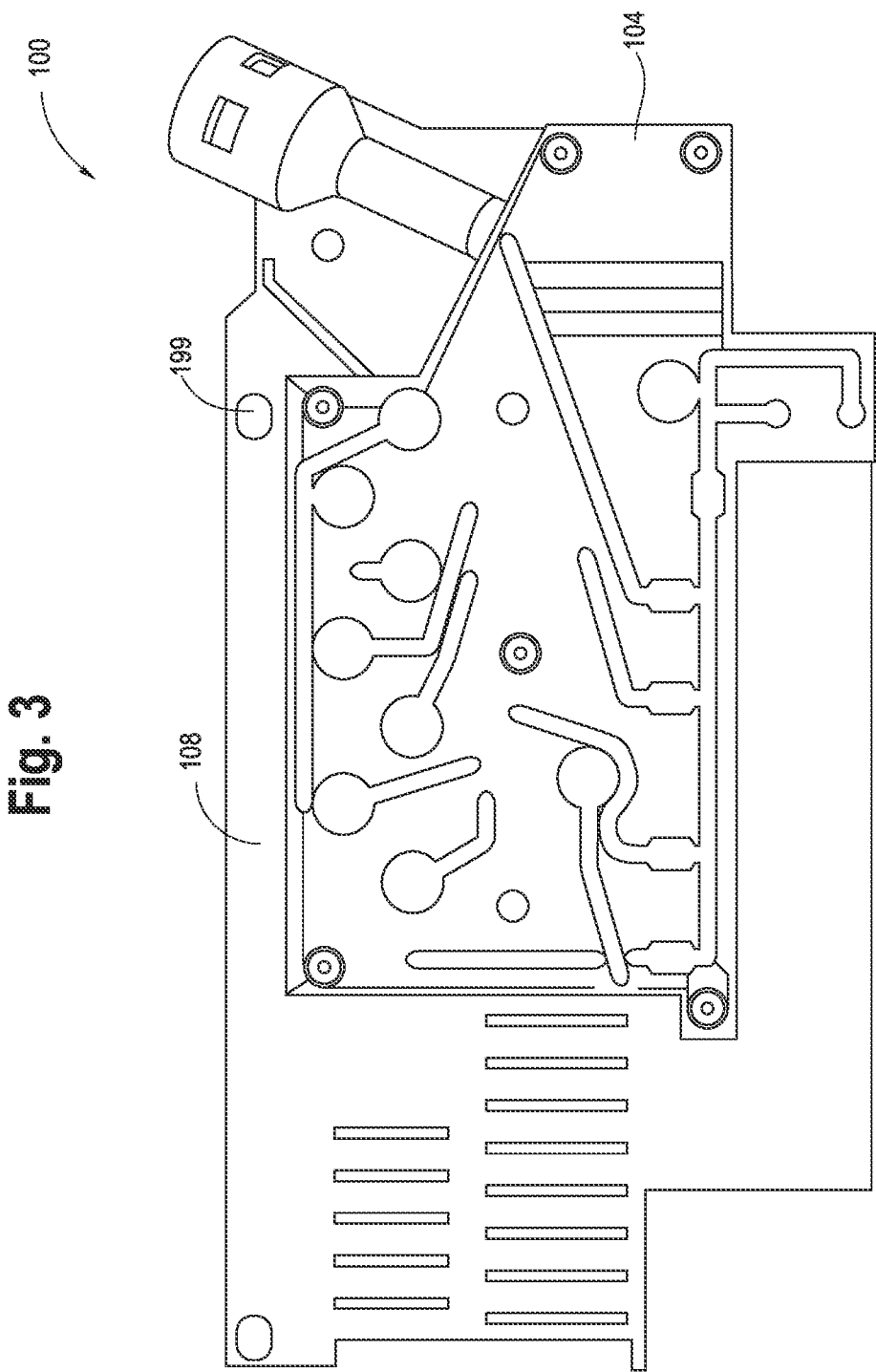
FIG. 3 illustrates a rear view of the microfluidic device of FIG. 1.

FIGS. 1-3 illustrate an exploded perspective view, a frontal (top) view, and a rear (bottom) view, respectively, of a microfluidic device 100 for performing an assay (e.g., a multiplex diagnostic of influenza (Flu) and Respiratory Syncytial Virus (RSV), such as a Flu/RSV assay). The microfluidic device 100 can be coupled to a reader that controls certain functionalities (e.g., valve configurations, mixing operations, heating, pumping, and monitoring of such functions) of the microfluidic device 100. The microfluidic device 100 includes a cartridge assembly 102, an elastomer layer 104, and a lid 106. The cartridge assembly 102 and the elastomer layer 104 together provide a series of fluidly coupled ports, channels, chambers, reservoirs, valves, and accessory components by which the assay can be carried out to detect the presence of one or more target nucleic acids in a sample provided to the microfluidic device 100. The lid 106 covers the cartridge assembly 102 and provides a layer through which the one or more target nucleic acids can be detected within the cartridge assembly 102. The cartridge assembly 102 includes a cartridge 108 and several accessory components (not shown in FIGS. 2 and 3) including a cap 110, a seal 112 (e.g., an o-ring seal), four plugs 114, a first magnet 116, an optional second magnet 118, multiple (e.g., eight) third magnets 120, a first reaction pellet 122, an optional intermediary pellet 123, and multiple (e.g., eight) second reaction pellets 124.

Figure 4:
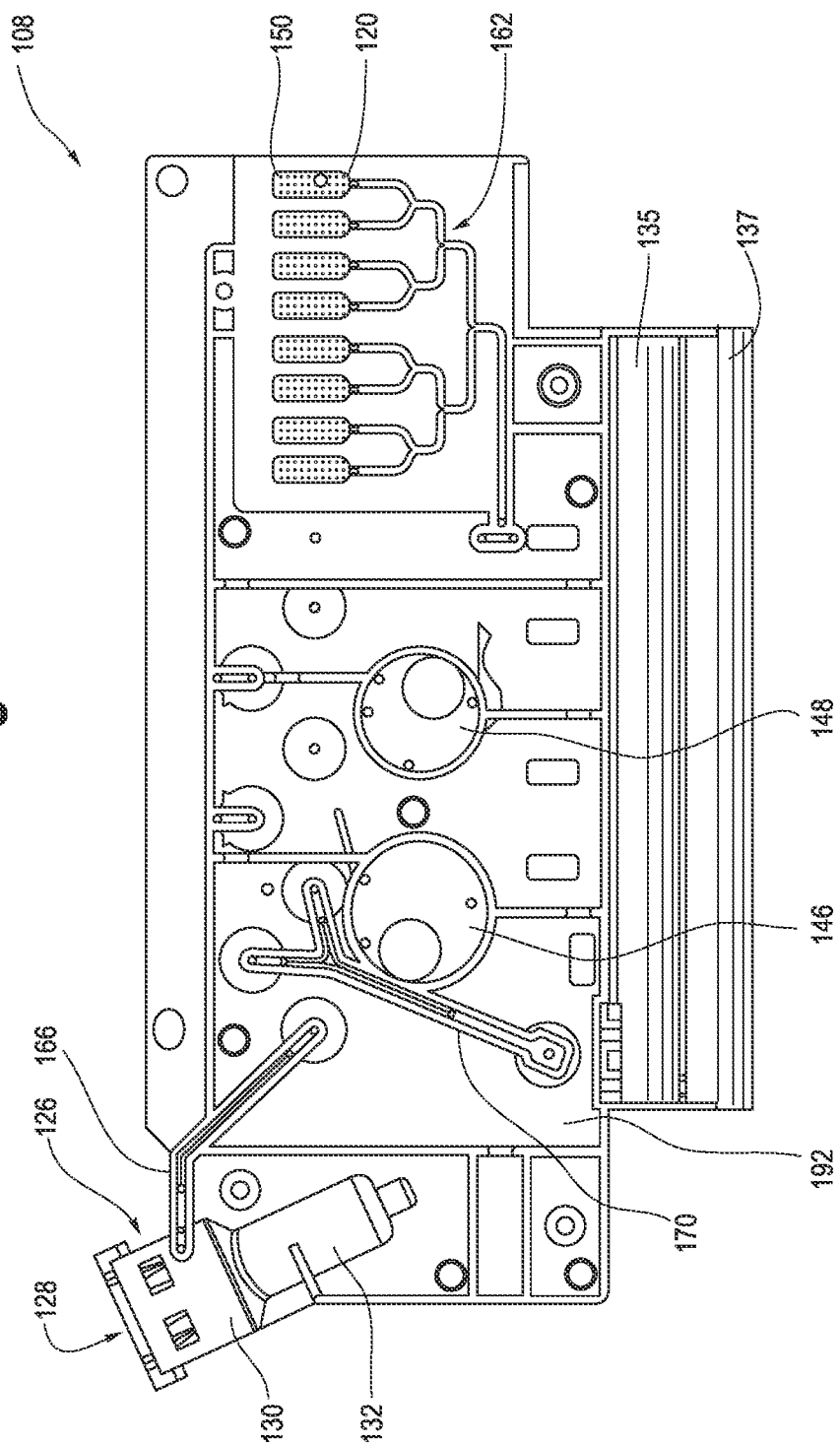
FIG. 4 illustrates a top view of a cartridge of the microfluidic device of FIG. 1.
Figure 5:
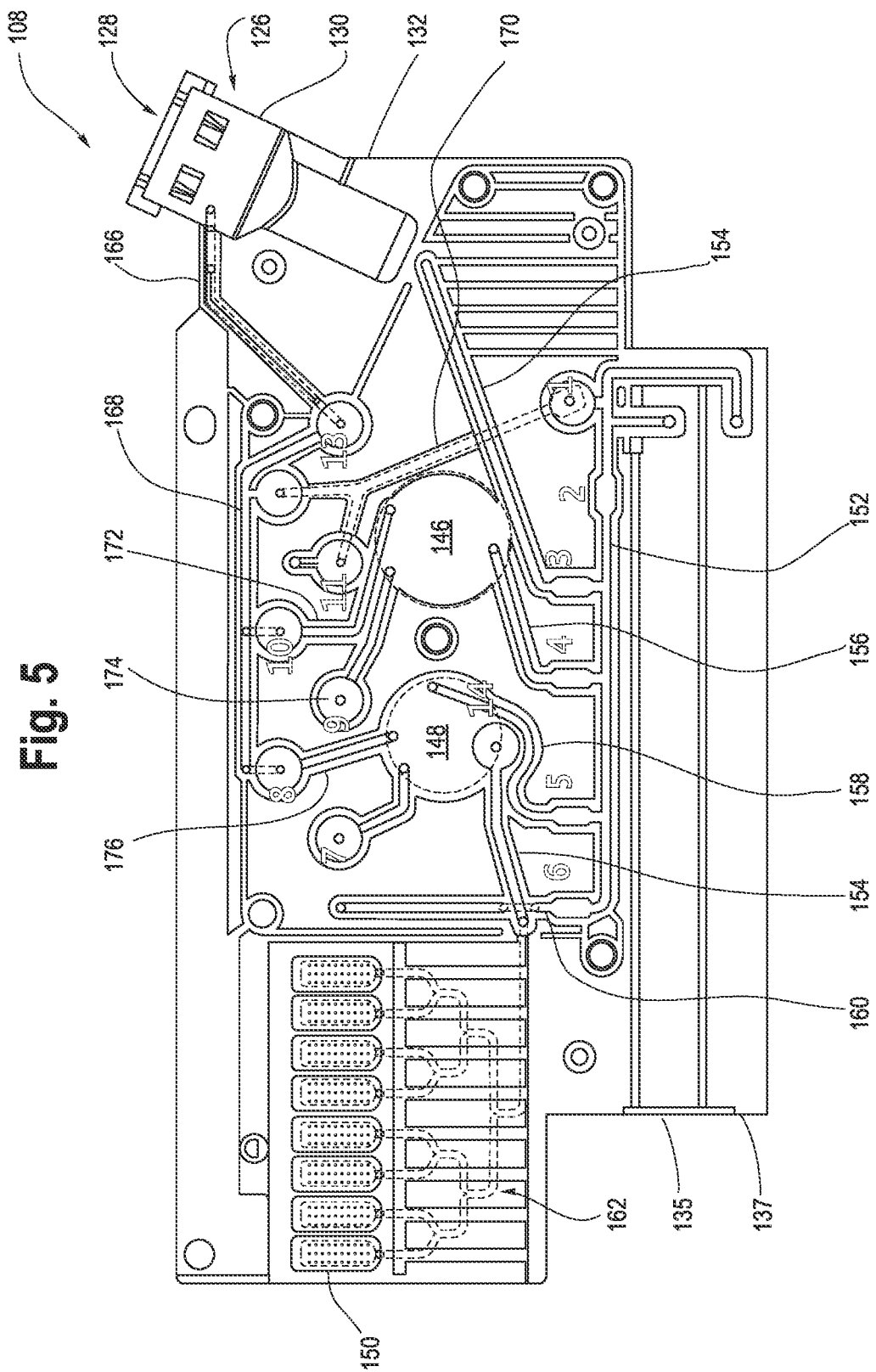
FIG. 5 illustrates a bottom view of the cartridge of the FIG. 4.

FIGS. 4 and 5 illustrate top and bottom views, respectively, of the cartridge 108. The cartridge 108 defines a geometry of a microfluidic network through which fluids flow during the assay. The cartridge 108 defines a sample chamber 126 that forms an opening 128. The sample chamber 126 provides an inlet port to the microfluidic network and is sized and shaped to accommodate various sample collection devices, such as swabs (e.g. cotton swabs) and collection tubes. For example, the sample chamber 126 includes a relatively wide first portion 130 and a relatively narrow second portion 132. The first portion 130 has a length of about 5 mm to about 20 mm (e.g., about 13 mm) and a relatively large internal diameter of about 8 mm to about 20 mm (e.g., about 16 mm), such that the first portion 130 can accommodate widely used sample collection swabs or tubes. The first portion 130 narrows to the second portion 132, which has a length of about 10 mm to about 30 mm (e.g., about 16 mm) and a relatively small internal diameter of about 6 mm to about 10 mm (e.g., about 8 mm), such that a tip of a swab within the sample chamber 126 is completely wetted when a liquid reagent is delivered to the sample chamber 126. The cap 110 and the seal 112 of the cartridge assembly 102 are sized to be inserted (e.g., with the seal 112 surrounding the cap 110) into the opening 128 of the sample chamber 126 to close and hermetically seal the sample chamber 126.

Figure 6A:
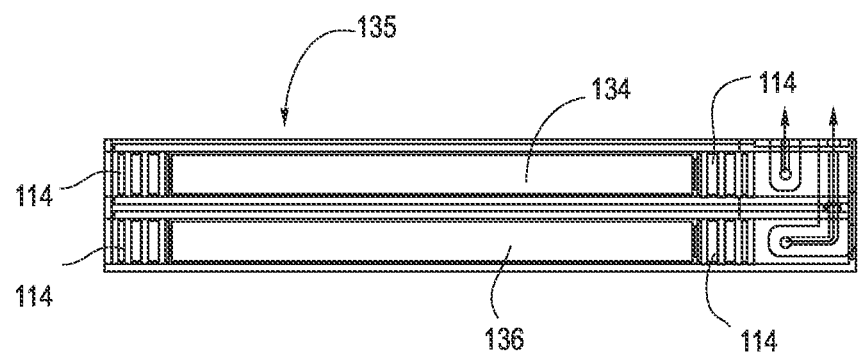
FIG. 6 illustrates a cross-sectional view of pumping chambers of the cartridge of FIG. 4.
Figure 6B:
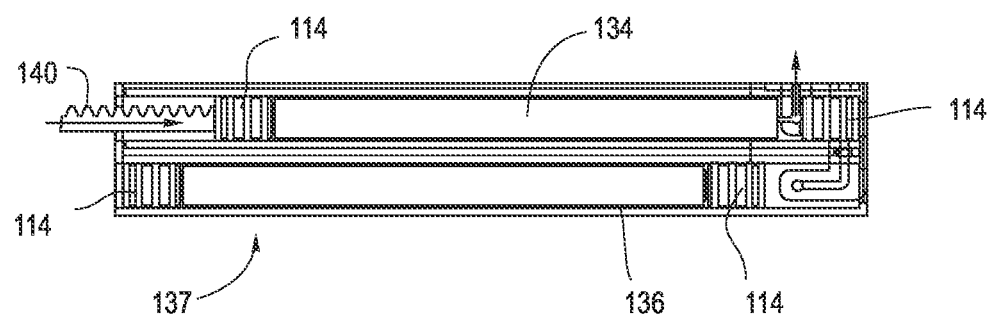
Figure 7:
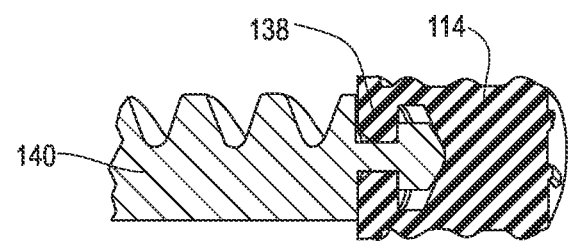
FIG. 7 illustrates a cross-sectional view of a plug within a pumping chamber of FIG. 6.

The cartridge 108 also defines a first pumping chamber 134 and a second pumping chamber 136. FIG. 6 illustrates a cross-sectional view of the first and second pumping chambers 134, 136. A plug 114 is disposed within each end region of the first and second pumping chambers 134, 136. FIG. 7 illustrates a cross-sectional view of one of the plugs 114 located remote from the microfluidic network (i.e., the plugs 114 on the left side of FIG. 6). Each plug 114 defines an undercut 138 that is formed to engage (e.g., retain) a rod 140 of the reader to allow the rod to apply a force to (e.g., to push or pull) the plug 114 to force fluid within the pumping chambers 134, 136 into the microfluidic network or to withdraw fluid from the microfluidic network into the pumping chambers 134, 136. The pumping chambers 134, 136, each together with two plugs 114, respectively form first and second pumps 135, 137 (e.g., on-board, integrated syringe pumps) that are actuated by rods 140 of the reader to drive fluid flows within the microfluidic network.

In an initial, closed state (a) of the first and second pumps 135, 137, the plugs 114 located adjacent the microfluidic network block fluid communication between ports 142, 144 of the pumping chambers 134, 136 and the microfluidic network. In an actuated state (b) of the first and second pumps 135, 137, the plugs 114 located adjacent the microfluidic network enable fluid communication between the ports 142, 144 of the pumping chambers 134, 136 and the microfluidic network. Each pumping chamber 134, 136 has a length of about 50 mm to about 100 mm (e.g., about 80 mm) and an internal diameter of about 4 mm to about 8 mm (e.g., about 6 mm). Excluding volumes of the plugs 114, each of the pumping chambers 134, 136 can accommodate a fluid volume of about 1 mL to about 5 mL (e.g., about 2 mL).

Referring again to FIGS. 4 and 5, the cartridge 108 defines a first reaction chamber 146 that is primed with the first reaction pellet 122 and that houses the first magnet 116. The first reaction chamber 146 has an internal diameter of about 15 mm to about 20 mm (e.g., about 18 mm) and a volume of about 1 mL to about 2 mL (e.g., about 1.6 mL). The cartridge 108 further defines a mixing chamber 148 that houses the second magnet 118 and the intermediary pellet 123. The mixing chamber 148 has an internal diameter of about 12 mm to about 18 mm (e.g., about 15 mm) and a volume of about 0.7 mL to about 1.7 mL (e.g., about 1.1 mL). The first magnet 116 can be actuated (e.g., rotated) by the reader to dissolve the first reaction pellet 122 in a liquid reagent within the first reaction chamber 146. The second magnet 118 can be actuated (e.g., rotated) by the reader to mix fluids within the mixing chamber 148. The first reaction chamber 146 and the mixing chamber 148 can withstand a magnet spin speed of up to about 60 rad/s. During the assay, the first and second magnets 116, 118 may be spun by the reader at angular speeds in a range of about 6 rad/s to about 30 rad/s. Additionally, the first reaction chamber 146 and the mixing chamber 148 can withstand a temperature of up to about 80° C. and may be heated by respective adjacent heating elements of the reader to temperatures between about 37° C. and about 60° C. during the assay.

The cartridge 108 also defines a set of multiple (e.g., eight) second reaction chambers 150 such that multiplexing can be carried out within the microfluidic device 100. Each second reaction chamber 150 is primed with a second reaction pellet 124 and houses an optional third magnet 120. Each second reaction chamber 150 has an internal width of about 2.0 mm to about 4.0 mm (e.g., about 3.0 mm), an internal length of about 5.0 mm to about 15.0 mm (e.g., about 10.0 mm), and an internal depth of about 1.0 mm to about 3 mm (e.g., about 2.2 mm), such that each second reaction chamber 150 has a volume of about 10 µL to about 200 µL (e.g., about 66 µL). In some embodiments, the third magnets 120 are actuated (e.g., rotated) by the reader to dissolve the second reaction pellets 124 in liquid reagents within the second reaction chambers 150. The second reaction chambers 150 can withstand a magnet spin speed of up to about 60 rad/s. In some examples, the third magnets 120 can move vertically in the second reaction chambers 150 at a rate of up to about 5 Hz. During the assay, the third magnets 120 may be spun by the reader at angular speeds in a range of about 6 rad/s to about 30 rad/s or may be pulled up and down in the chamber at a rate of about 1 Hz to about 5 Hz. Additionally, the second reaction chambers 150 can withstand a temperature of up to about 80° C. and may be heated by respective adjacent heating elements of the reader to temperatures between about 37° C. and about 60° C. during the assay. In addition to or alternatively to mixing in the second reaction chambers 150 with the third magnets 120, mixing in the second reaction chambers 150 may be achieved by acoustic microstreaming.

Figure 8:
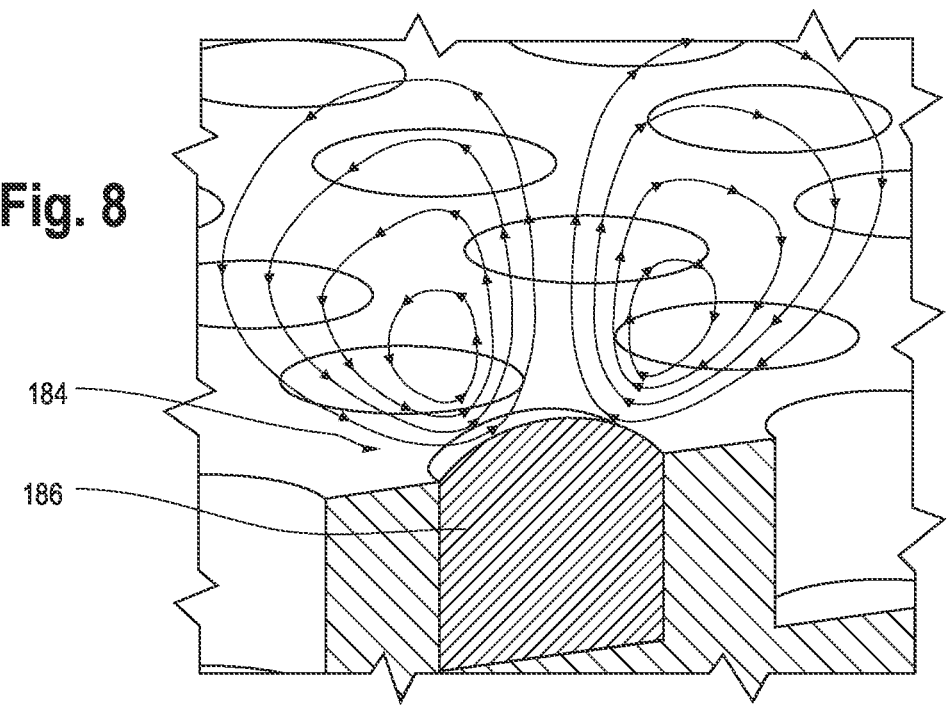
FIG. 8 illustrates a cross-sectional side view of a reaction chamber of the cartridge of FIG. 4.
Figure 9:
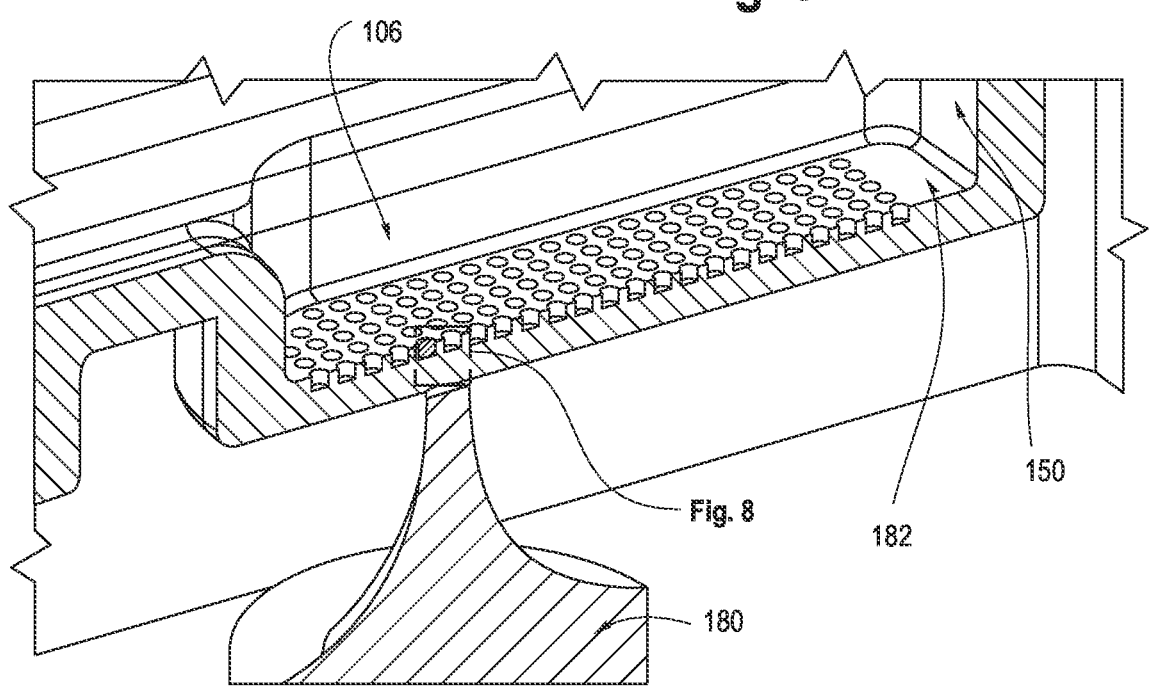
FIG. 9 illustrates a cross-sectional perspective view of the reaction chamber of FIG. 8.
Figure 10A:
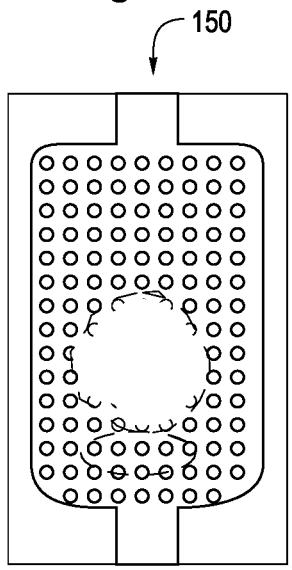
FIG. 10 illustrates a top view of the reaction chamber of FIG. 8.
Figure 10B:
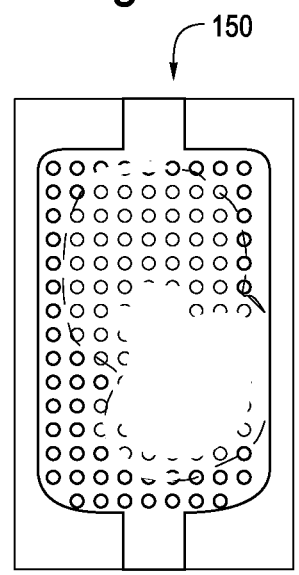
Figure 10C:
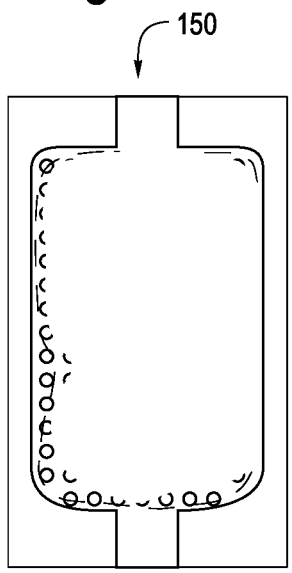
Figure 10D:
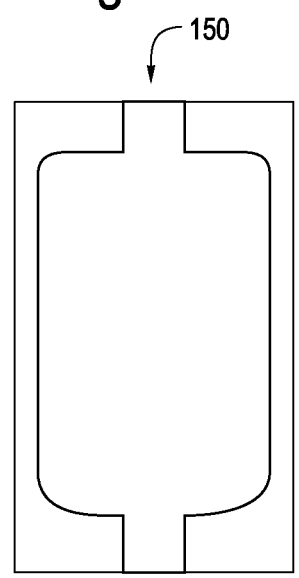

FIGS. 8, 9, and 10 illustrate a cross-sectional side view, a cross-sectional perspective view, and top views, respectively, of a second reaction chamber 150. Acoustic microstreaming may be used to accomplish mixing in the second reaction chambers 150 as a result of a piezoelectric transducer or a sonotrode in the reader that acts on air pockets formed by cavities 184 disposed along bottom surfaces 182 of the second reaction chambers 150 or above the second reaction chambers 150 atop the lid 106 covering the cartridge 108. The multiple cavities 184 extend from the bottom surfaces 182 of the second reaction chambers 150. The filling of the chamber with fluid causes microbubbles 186 to be trapped in the cavities 184 of the second reaction chambers 150. Surfaces of the trapped microbubbles 186 oscillate as a result of the action of the ultrasonic transducer. The movement of the microbubble surfaces (e.g., bubble "skin") causes movement of the liquid in contact with the microbubbles 186. These resulting oscillations at the applied acoustic frequency cause $2^{nd}$ order flows that resemble microvortices within the fluid volume. FIG. 10 illustrates four successive images of mixing occurring via acoustic microstreaming in a second reaction chamber 150. As shown, nearly complete mixing may be achieved within a second reaction chamber 150 within about 7 seconds.

In addition to housing an optional third magnet 120, each of the second reaction chambers 150 includes an identical air spring that permits an even distribution of fluid within the second reaction chambers 150. Since each of the second reaction chambers 150 contains its own air spring, a filling level among the second reaction chambers 150 automatically equilibrates as a result of backpressure that is generated as the second reaction chambers 150 fill with fluid. Accordingly, the second reaction chambers 150 can fill with precise, accurate, equivalent volumes of fluid and achieve an equivalent pressure.

Referring again to FIGS. 4 and 5, the cartridge 108 defines multiple fluid channels of the microfluidic network. Additionally, a volume formed between the cartridge 108 and the lid 106 and external to the microfluidic network defined by the cartridge 108 provides a waste reservoir 192 (e.g., an air reservoir) that buffers an air pressure in the microfluidic network, such that the microfluidic device 100 does not need to include a separate pressure equilibration mechanism. The cartridge 108 defines a fluid channel 152 extending from the pumping chambers 134, 136, a fluid channel 154 extending from the second portion 132 of the sample chamber 126 to the fluid channel 152, a fluid channel 156 extending from the fluid channel 152 to the first reaction chamber 146, a fluid channel 158 extending from the fluid channel 152 to the mixing chamber 148, a terminal fluid channel 160 that extends from the fluid channel 152, a fluid channel network 162 feeding into the second reaction chambers 150, a fluid channel 164 extending from the mixing chamber 148 to the fluid channel network 162, a fluid channel 166 extending from the first portion 130 of the sample chamber 126, a fluid channel 168 extending from the fluid channel 166, a forked fluid channel 170 extending from the pumping chambers 134, 136 to the fluid channel 168 and to the waste reservoir 192, a fluid channel 172 extending from the first reaction chamber 146 to the fluid channel 168, a fluid channel 174 extending from the first reaction chamber 146 to the waste reservoir 192, a fluid channel 176 extending from the mixing chamber 148 to the fluid channel 168, and a fluid channel 178 extending from the mixing chamber 148 to the waste reservoir 192. The various channels 152-178 have internal widths in a range of about 1.0 mm to about 2.5 mm and cross-sectional areas in a range of about 0.5 mm$^2$ to about 1.5 mm$^2$.

Figure 11:
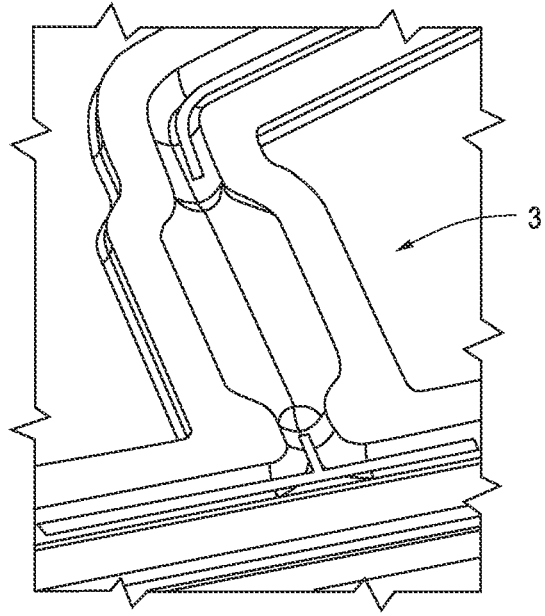
FIG. 11 illustrates a top view of a valve along the cartridge of FIG. 4.
Figure 12:
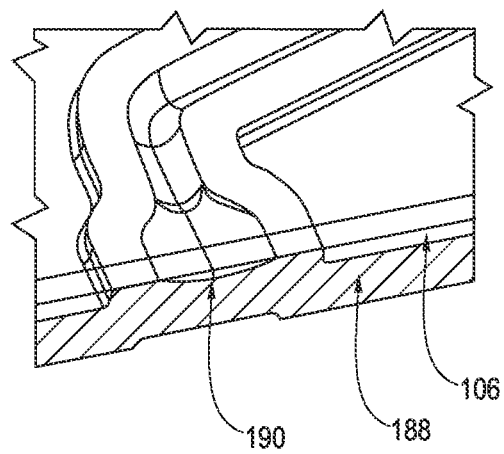
FIG. 12 illustrates a perspective cross-sectional view of the valve of FIG. 11.

The cartridge 108, together with the elastomer layer 104, further defines a series of valves 1-13 along the microfluidic network. The valves 1-6 are formed as channel valves, while the valves 7-13 are formed as paging valves. FIGS. 11 and 12 illustrate top and perspective cross-sectional views valves along the cartridge 108. Certain cavities within the cartridge 108 and corresponding regions of the elastomer layer 104 lying along the cavities can cooperate to form valves at selected locations along the microfluidic network. For example, a region 188 of the elastomer layer 104 lying along a cavity 190 of the cartridge 108 cooperate to form the valve 3. In an open state of the valve 3 (as shown in FIGS. 11 and 12), the region 188 is spaced apart from a surface of the cavity 190 such that fluid is permitted to pass through the cavity 190 between fluid channels coupled to opposite ends of the cavity 190. At desired points during the assay, a piston of the reader can apply a force to the region 188 to push the region 188 into the cavity 190 and in contact with the cavity 190 to block fluid from flowing through the cavity 190 between fluid channels coupled to opposite ends of the cavity 190, thereby closing valve 3. In a closed state of the valves 1-13, the cavities do not exist (i.e., the cavities do not have any depth). In an open state of the valves, fluid flow forces the valves open (i.e., the fluid flow provides depth to the cavities). Accordingly, the cavities along the cartridge 108 may have depths in a range of about 0 μm to about 750 μm, and the reader may apply forces in a range of about 6 N to about 8 N to achieve adequate contact between the regions of the elastomer layer 104 and the adjacent cavities of the cartridge 108 to close the valves.

The elastomer layer 104 and the lid 106 are attached to the cartridge 108 along peripheral edges and at one or more interior locations along the elastomeric gasket (e.g., as shown by the dark lines in FIGS. 2 and 3) via various joining mechanisms (e.g., laser welding, ultrasonic welding, gluing, thermal welding, and some fastening mechanisms) such that the microfluidic device 100 is hermetically sealed when the sample chamber 126 is closed with the cap 110. The microfluidic device 100 is a disposable unit that can be discarded after a single use (e.g., after being used to perform a single assay). The microfluidic device 100 has a compact footprint and a light weight of about 20 g to about 40 g such that the microfluidic device 100 can be easily handled, packaged, transported, and stored. The microfluidic device 100 may be provided as an assembled, ready-to-use device that is primed with pellets and reagents. The microfluidic device 100 may be provided within an atmospherically controlled packaging (e.g., a composite plastic/metal foil pouch) including moisture/oxygen absorbent pellet (e.g., for use with such sensitive components). The microfluidic device 100 may have a shelf life of about 12 months to about 24 months, as dictated by the stability of the reagents (e.g., Recombinase Polymerase Amplification (RPA) reagents).

The cartridge 108 is a rigid structure that may be made of one or more chemically robust materials, such as polypropylene, polystyrene, polyester, polymethylmethacrylate, and polyetheretherketone. In some embodiments, the cartridge 108 has a total length (including an extent of the sample chamber 126) of about 80 mm to about 200 mm (e.g., about 150 mm). In some embodiments, the cartridge 108 has a total width (including an extent of the sample chamber 126) of about 50 mm to about 100 mm (e.g., about 80 mm). In some embodiments, the cartridge 108 has a total thickness (including an extent of the sample chamber 126) of about 8 mm to about 20 mm (e.g., about 16 mm). In some embodiments, the magnets 116, 118, 120 may be made of one or more chemically robust materials, such as neodymium, Teflon, or glass. In some examples, other inert materials may also be used to encapsulate the magnets 116, 118, 120. In some embodiments, metallic materials (e.g. iron, nickel, and alloys) that are attracted to an external magnetic field (i.e. from the rig) may be used in place of the magnets 116, 118, 120 in these locations. The cartridge 108 may be transparent or translucent at one or more portions (e.g., at the chambers 146, 148, 150) to allow visualization and/or detection. The cartridge 108 also defines one or more alignment holes 199 (e.g., shown in FIGS. 1-3) that are sized and positioned to locate the microfluidic device 100 within the reader. For example, associated pins within the reader are positioned to engage the alignment holes 199 of the cartridge.

In some embodiments, the cap 110 and the seal 112 may be made of one or more chemically robust materials, such as polypropylene or nitrile-butadiene rubber. In some embodiments, the seal 112 may be plastic-on-plastic or made with an overmolded thermoplastic elastomer. In some embodiments, the plugs 114 may be made of bromobutyl or another material. Owing at least in part to a chemical robustness of the cartridge 108 and the plugs 114, the pumps 135, 137, when used as liquid reservoirs, have been found to achieve an average water vapor transmission (e.g., diffusion) rate as low as about 0.00054 g/(package*day).

The elastomer layer 104 may be made of one or more chemically robust materials, such as a thermoplastic elastomer. According to such a material formulation, the elastomer layer 104 can elastically (e.g., reversibly) deform to close and open the valves 1-13. In some embodiments, the elastomer layer 104 has a total length of about 50 mm to about 150 mm (e.g., about 100 mm). In some embodiments, the elastomer layer 104 has a total width of about 20 mm to about 80 mm (e.g., about 50 mm). In some embodiments, the elastomer layer 104 has a total thickness of about 0.5 mm to about 1.5 mm (e.g., about 1.0 mm).

The lid 106 may be made of one or more materials including polypropylene or polycarbonate. The lid 106 is transparent or translucent to allow visualization and detection of reactions occurring within the chambers 146, 148, 150 of the cartridge 108. In some embodiments, the lid 106 has a total length of about 50 mm to about 200 mm (e.g., about 130 mm). In some embodiments, the lid 106 has a total width of about 20 mm to about 80 mm (e.g., about 50 mm). In some embodiments, the lid 106 has a total thickness of about 0.5 mm to about 1.0 mm (e.g., about 0.7 mm).

As discussed above, the microfluidic device 100 is configured (e.g., has a size, a shape, and a material constituency) to be used with a reader that can receive the microfluidic device 100. The reader can receive the microfluidic device 100 within a test port. The reader is configured to interact with microfluidic device 100 during operation of an assay within the microfluidic device 100. A series of actuators contact the microfluidic device 100 in proximity of the various valve structures to effectively "open and close" the valves. As discussed above, typically, when an actuator compresses the elastomer layer 104 against the underlying molded cartridge 108, a valve will be in a closed state. Accordingly, when an actuator is released, the elastomer layer 104 relaxes and thereby allows the valve to revert to an open state. The reader also includes heater elements that apply localized heating to regions of the microfluidic device 100, as may be required during performance of the assay. The reader also includes actuators that can push and pull the plungers of each pump (e.g., the rods 140), in order to achieve desired fluid movement within the microfluidic network. The reader also includes fluorescence detection optics that interrogate respective reaction chambers in order to provide measurement values that indicate presence or absence of target species within the sample under test. The reader may additionally include a bar code or a similar system for identification of a test type to ascertain whether the microfluidic device is within a prescribed use-by date range and to associate test results with electronic patient records.

Figure 13:
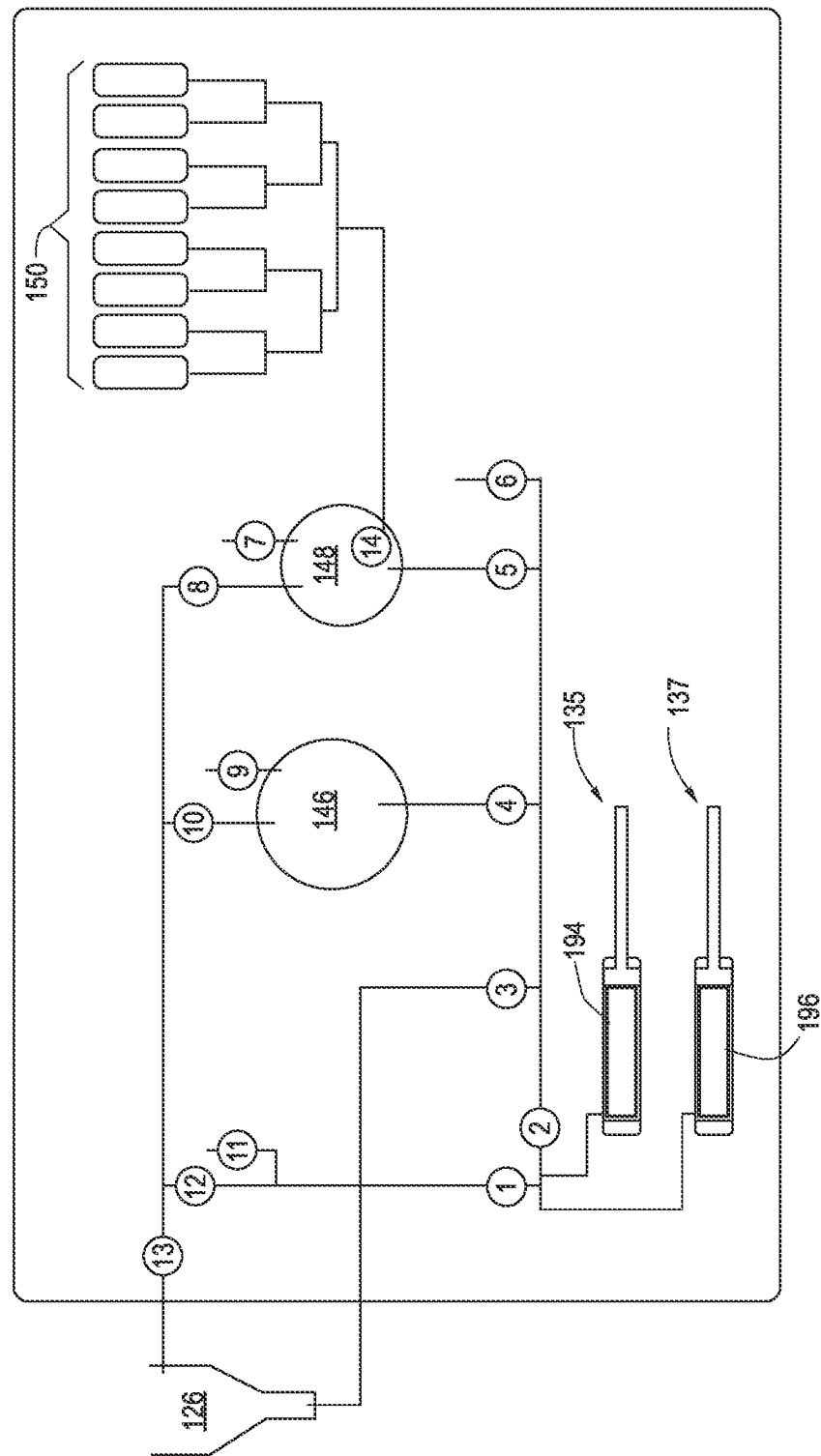
FIGS. 13-23 illustrate a sequence of schematic drawings of the cartridge of FIG. 4 that correspond to a method of performing an assay using the microfluidic device of FIG. 1.

FIGS. 13-23 illustrate sequential schematic drawings of the cartridge 108 that correspond to a method of performing an assay to detect a target nucleic acid using the microfluidic device 100. In some implementations, the assay is a Flu/RSV assay that is performed at isothermal conditions. Referring first to FIG. 13, the sample chamber 126 of the cartridge 108 is uncapped prior to a start of the assay such that the microfluidic device 100 is open to an ambient environment. The first pump 135 is in a closed state and is primed with about 1 mL to about 5 mL (e.g., about 2 mL) of a first liquid reagent 194 shown in the color blue. In some implementations, the first liquid reagent 194 is a lysis buffer and includes a catalytic agent, such as magnesium. In some implementations, the lysis buffer is an enzymatic lysing agent. In some implementations, the lysis buffer includes hydrochloric acid (HCL) at a concentration of about 10 mM to about 10 mM and TritionX100 at a concentration of about 0.1% to about 1%.

Still referring to FIG. 13, the second pump 137 is in a closed state and is primed with about 1 mL to about 5 mL (e.g., about 2 mL) of a second liquid reagent 196 shown in the color green. In some implementations, the second liquid reagent 196 is a typically the reaction buffer and has a pH near neutral. The second liquid reagent may include a catalytic agent, such as magnesium. The first and second reaction chambers 146, 150 are respectively primed with the first and second reaction pellets 122, 124. In some implementations, each of the first and second reaction pellets 122, 124 includes one or more freeze-dried amplification reagents, such as RPA reagents, a catalytic reagent (e.g., magnesium), and oligomers. The RPA reagents may include primers specific for the target of interest, as well as at least one probe with a detectable label for visualization of the amplified target, if present. The probe typically includes a fluorophore and a quencher, which will be separate following cleavage by a nuclease when the probe hybridizes to complementary sequence, if present in the amplified sample mixture.

The microfluidic device 100 is inserted into the reader, and the reader is operated manually via one or more control elements (e.g., buttons and switches) to start the assay. At the beginning of the assay, the valves 1-13 are open during insertion of the cartridge 108 into the reader. The reader is subsequently controlled to actuate the valves 1-13, the pumps 135, 137, the magnets 116, 118, 120, and the piezoelectric transducers 180 (shown in FIG. 8) and to heat the chambers 146, 148, 150 at certain times for carrying out the assay using the microfluidic device 100.

Figure 14:
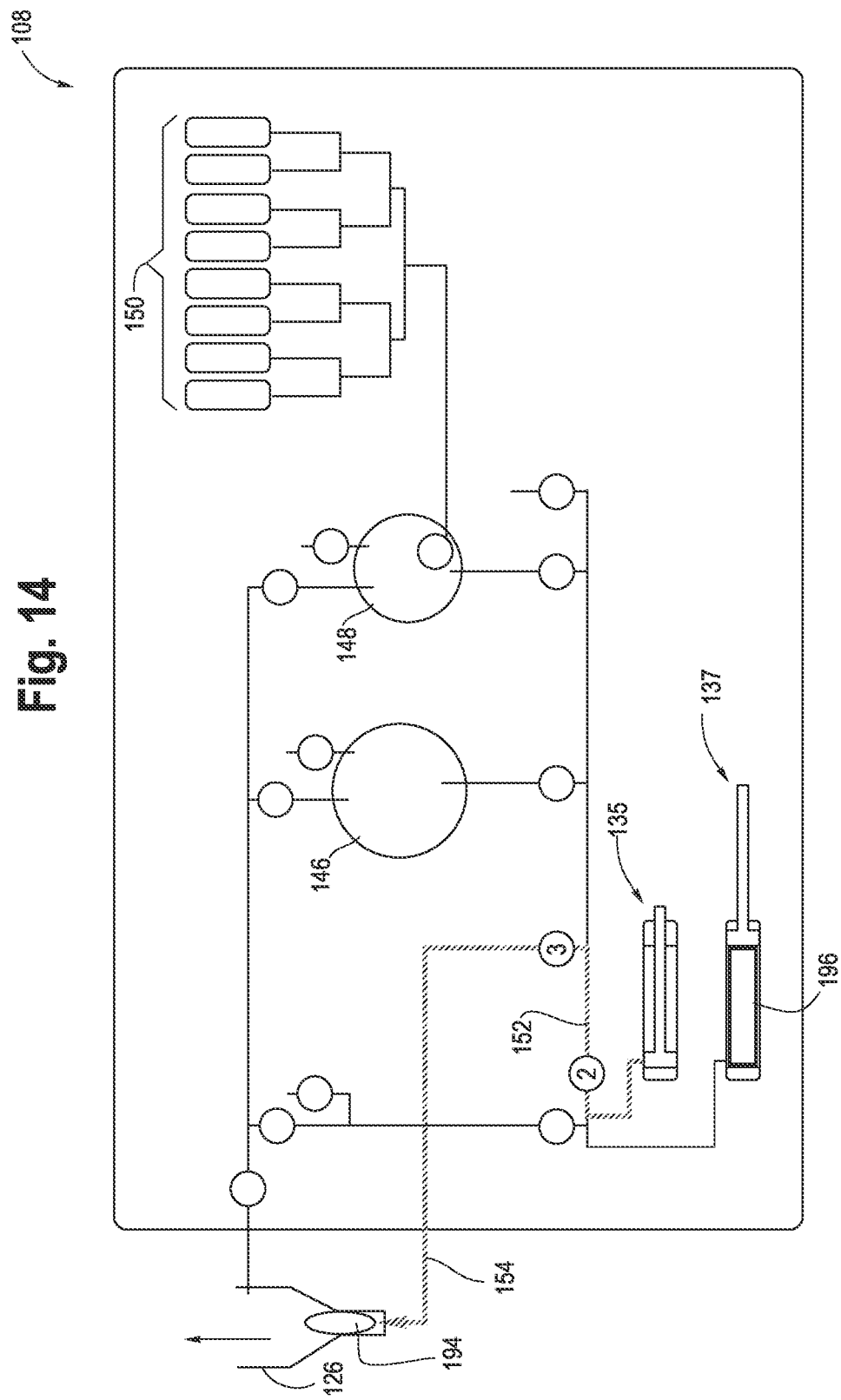
Figure 15:
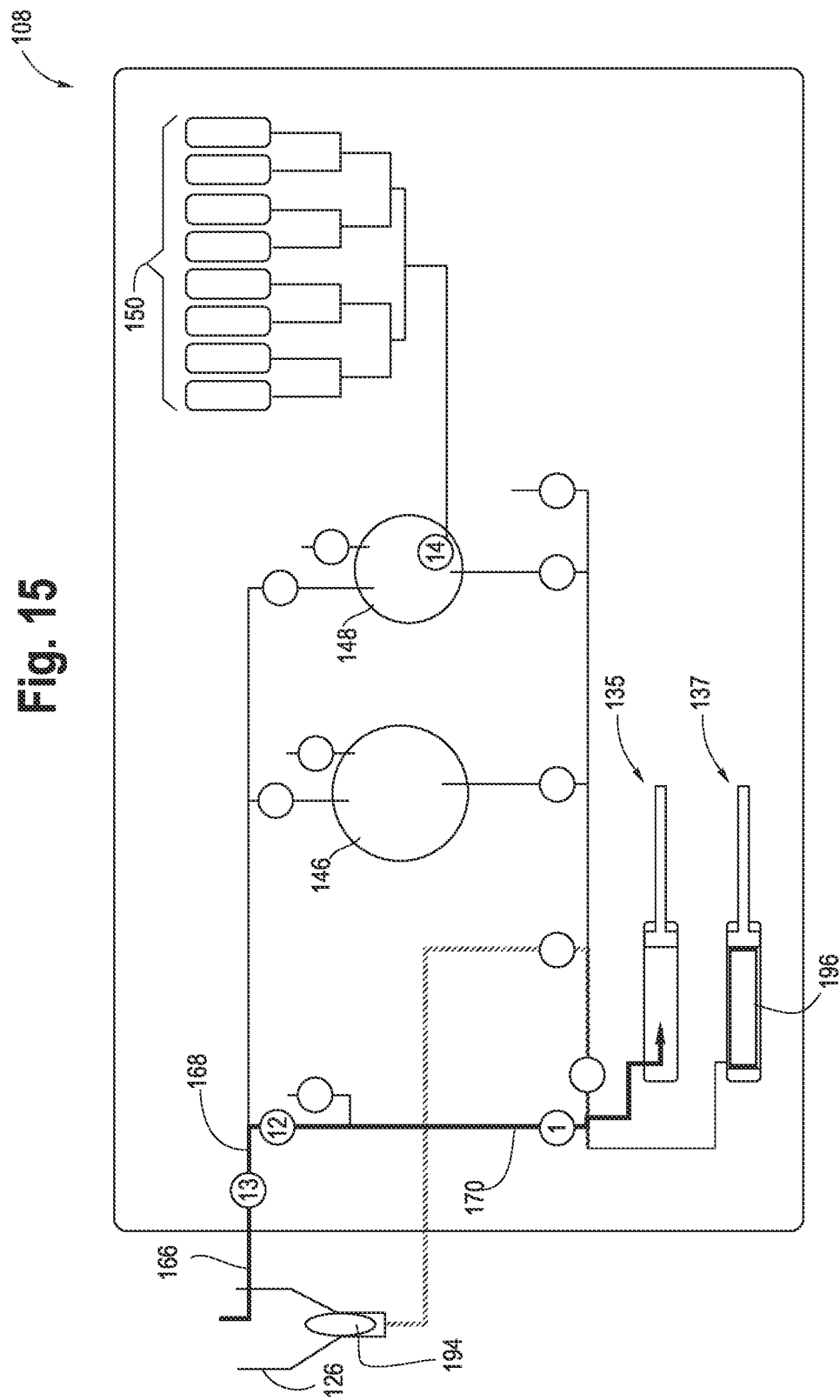

Referring to FIG. 14, the valves 2, 3 open, and the first pump 135 drives (e.g., pushes or forces) the first liquid reagent 194 from the first pumping chamber 134 to the sample chamber 126 via the fluid channels 152, 154 over a period of about 5 s to about 10 s (e.g., about 9 s). Referring to FIG. 15, the valves 2, 3 close, and the valves 1, 12, 13 open. The first pump 135 withdraws (e.g., pulls) about 1 mL to about 5 mL (e.g., about 2 mL) of air from the ambient environment into the pumping chamber 134 via the fluid channels 170, 168, 166 and the sample chamber 126 over a period of about 1 s to about 10 s (e.g., about 5 s).

Figure 16:
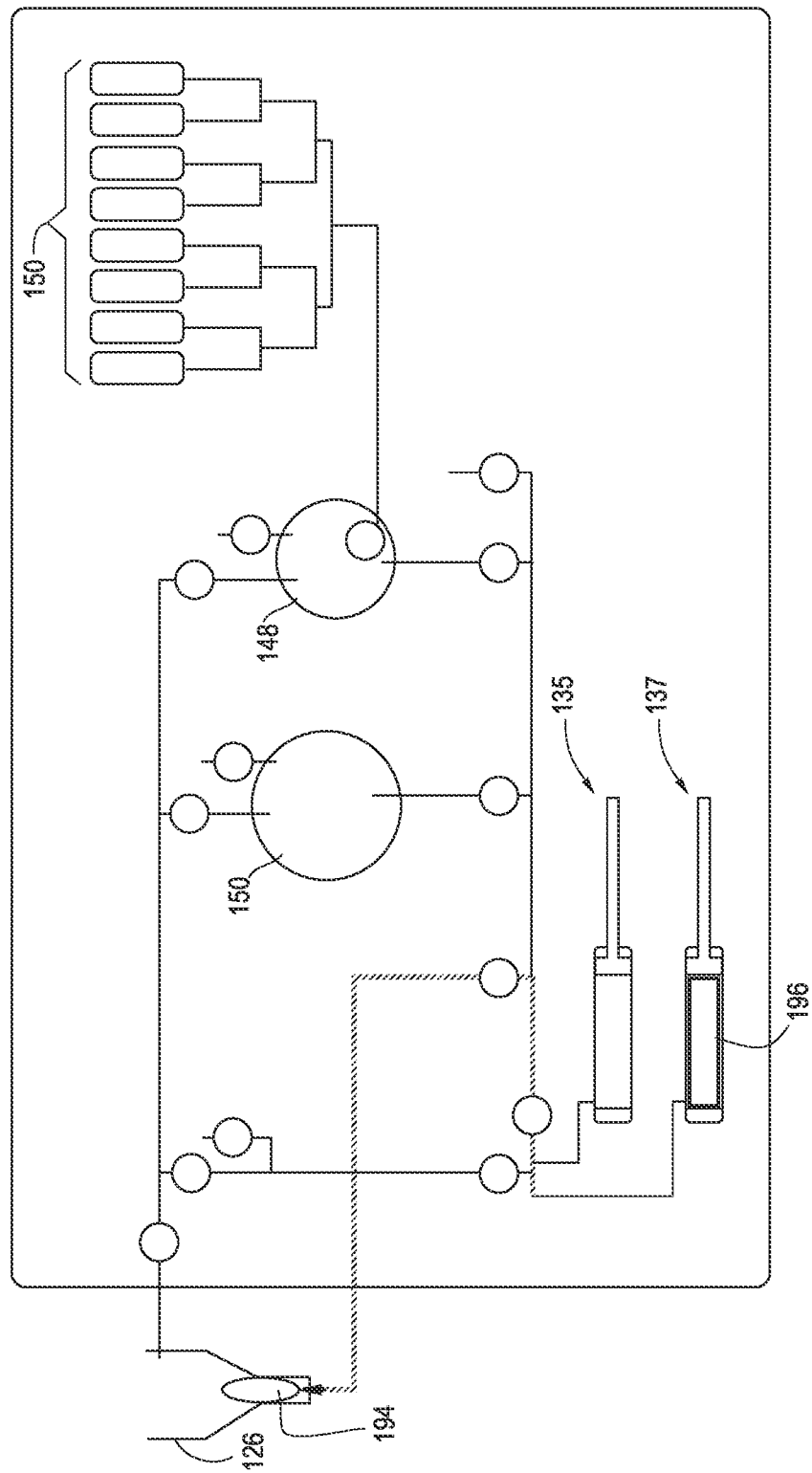

Referring to FIG. 16, the valves 1, 12, 13 close. A sample is delivered to the sample chamber 126 by a user, and the sample chamber 126 is closed and hermetically sealed with the cap 110 and the seal 112 by the user. In some implementations, the sample is a biological fluid or material collected from a human being or another animal. For example, the sample can include one or more of blood, sputum, mucus, saliva, tears, or urine. The sample can be acquired from the subject using a suitable sample collection device, such as a swab or collection tube. For example, swabs can be used to collect nasal, nasopharyngeal, vaginal, buccal, or meatal samples, and applied to ear, eye, throat, wound or other bodily surfaces. In some implementations, the sample can be delivered directly to the sample chamber 126 directly after the sample is collected from the subject with a sample collection device. In some implementations, the sample can be stored in viral transport media (VTM) or other liquid reagent following collection from the subject, and an aliquot of the stored sample can be delivered to the sample chamber 126 to initiate the assay. The sample, either as obtained from the subject or as stored in another medium, can be applied to the sample chamber 126 in substantially the same form as collected from the subject (e.g., without purification of the sample to isolate the target nucleic acids or to remove biological matrices or other constituents from the sample.)

In some implementations, the sample includes a target nucleic acid that includes a target polynucleotide sequence (e.g., or more than one target polynucleotide sequence, such as two or three target polynucleotide sequences). In some implementations, the target nucleic acid is a double-stranded DNA, a single stranded DNA, or RNA. In some implementations, the target nucleic acid is genomic DNA, plasmid DNA, viral DNA, mitochondrial DNA, cDNA, synthetic double-stranded DNA and synthetic single-stranded DNA. In some implementations, the target nucleic acid is viral DNA or viral RNA. In some implementations, the target nucleic acid is from an animal pathogen (e.g., a single-stranded DNA virus, a double-stranded DNA virus, a single-stranded RNA virus, or a bacterium). In some implementations, the animal pathogen is an influenza A virus, an influenza B virus, or RSV. In some implementations, the sample has been mixed with RPA reagents prior to being delivered to the sample chamber 126.

The sample mixes with about 400 µL to about 1500 µL (e.g., about 500 µL) of the first liquid reagent 194 contained in the sample chamber 126 for about 0 s to about 60 s (e.g., about 10 s). If the first liquid reagent 194 contains a lysing agent, the sample may be lysed during this mixing period. In some implementations, the sample chamber 126 may be heated during the mixing step. Once the sample is delivered to the sample chamber 126 and the cap is placed by the user, a seal integrity of the sample chamber 126 is tested by the reader.

Figure 17:
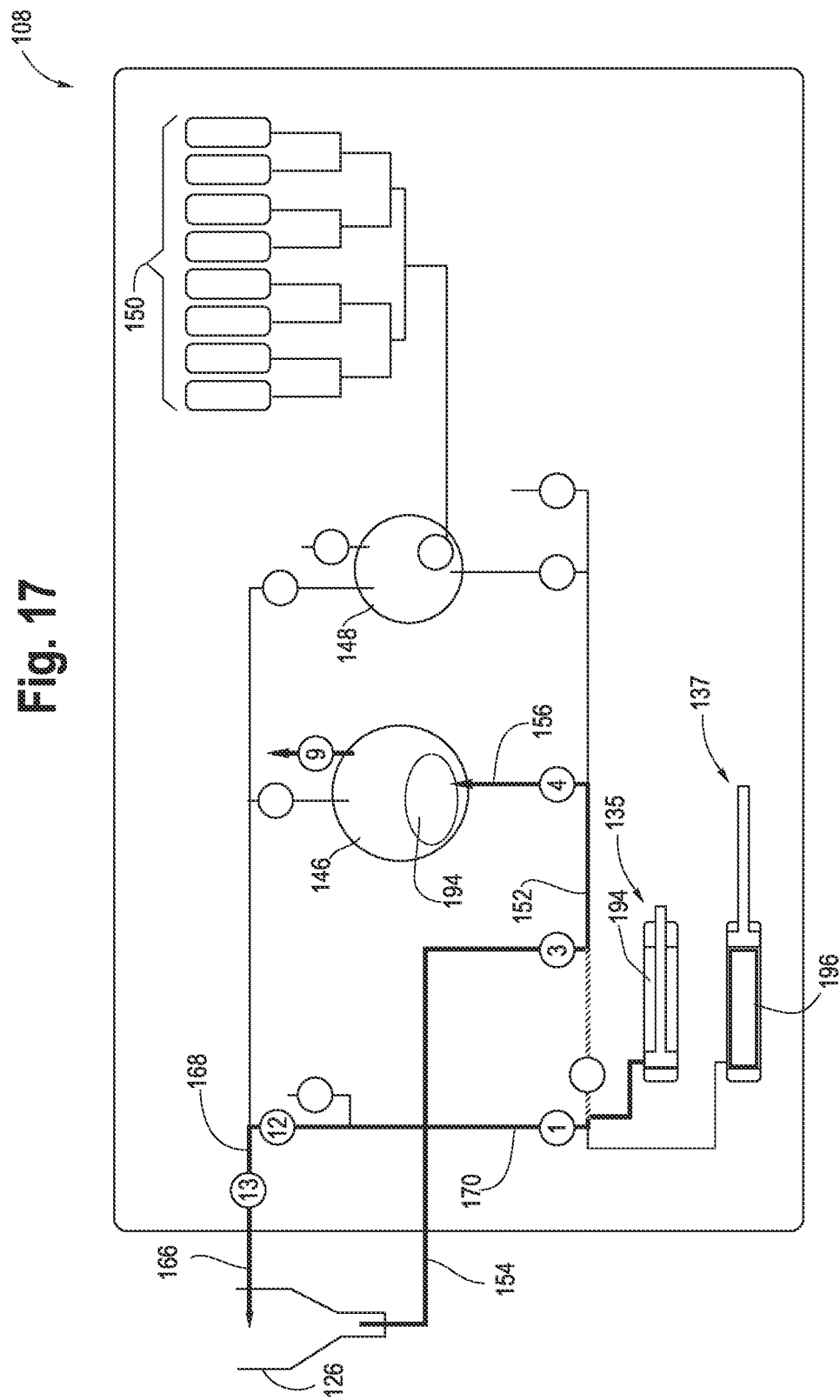

Referring to FIG. 17, the valves 1, 3, 4, 9, 12, 13 open, and the first pump 135 drives the air contained within the pumping chamber 134 to the sample chamber 126 via the fluid channels 170, 168, 166, thereby driving a volume of about 200 µL to about 1000 µL (e.g., about 500 µL) of the sample and the first liquid reagent 194 contained in the sample chamber 126 into the first reaction chamber 146 via the fluid channels 154, 152, 156 over a period of about 5 s to about 15 s (e.g., about 10 s). A first amplification reaction occurs in the first reaction chamber 146 to produce a first reaction product over a period of about 300 s to about 600 s (e.g., about 480 s). In some implementations, the first amplification reaction for amplifying the target polynucleotide sequence is an RPA reaction, and the first reaction product includes a first amplified polynucleotide sequence. During the first amplification reaction, the first reaction chamber 146 is heated, and the first magnet 116 in the first reaction chamber 146 rotates to dissolve the first reaction pellet 122 in the sample.

Figure 18:
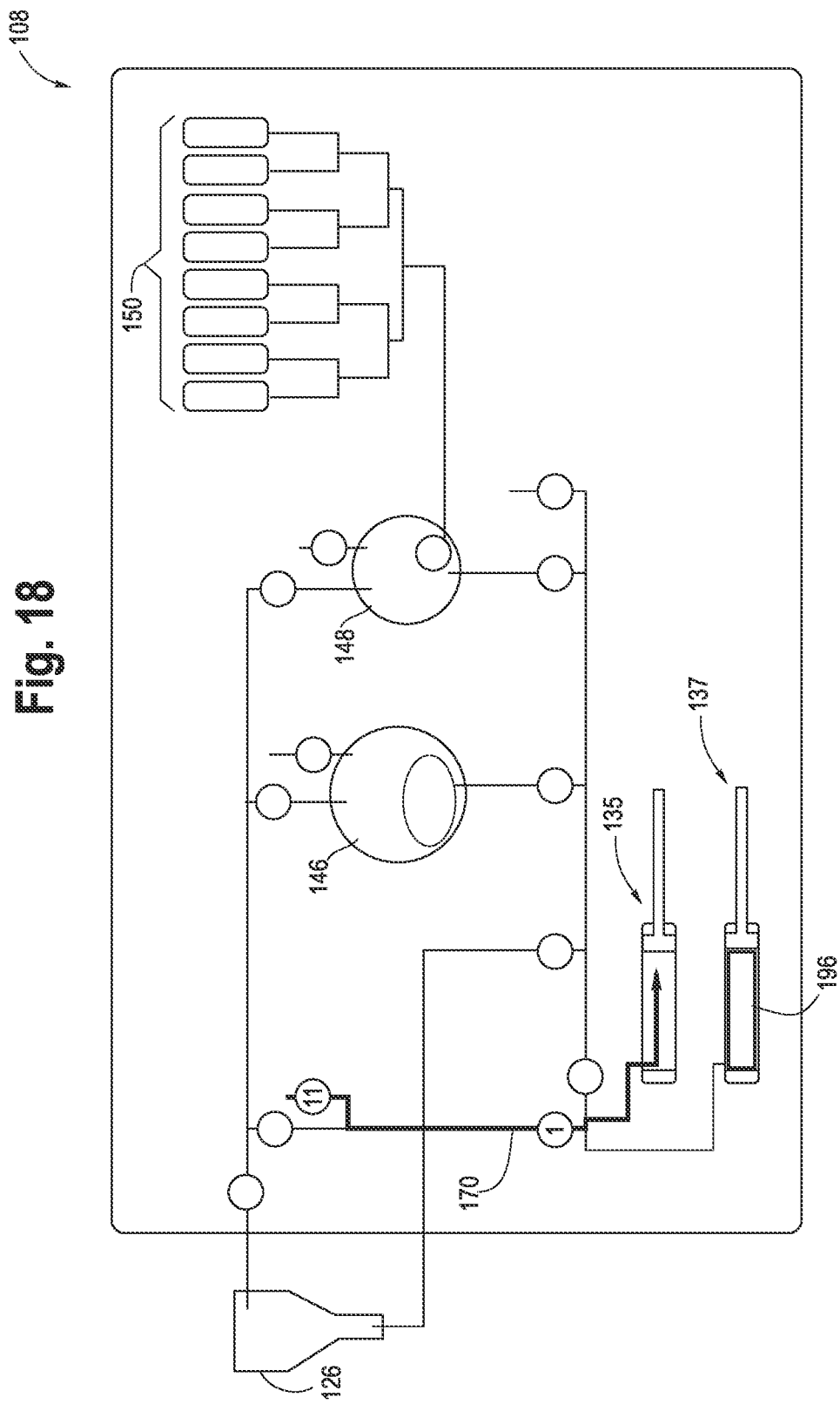
Figure 19:
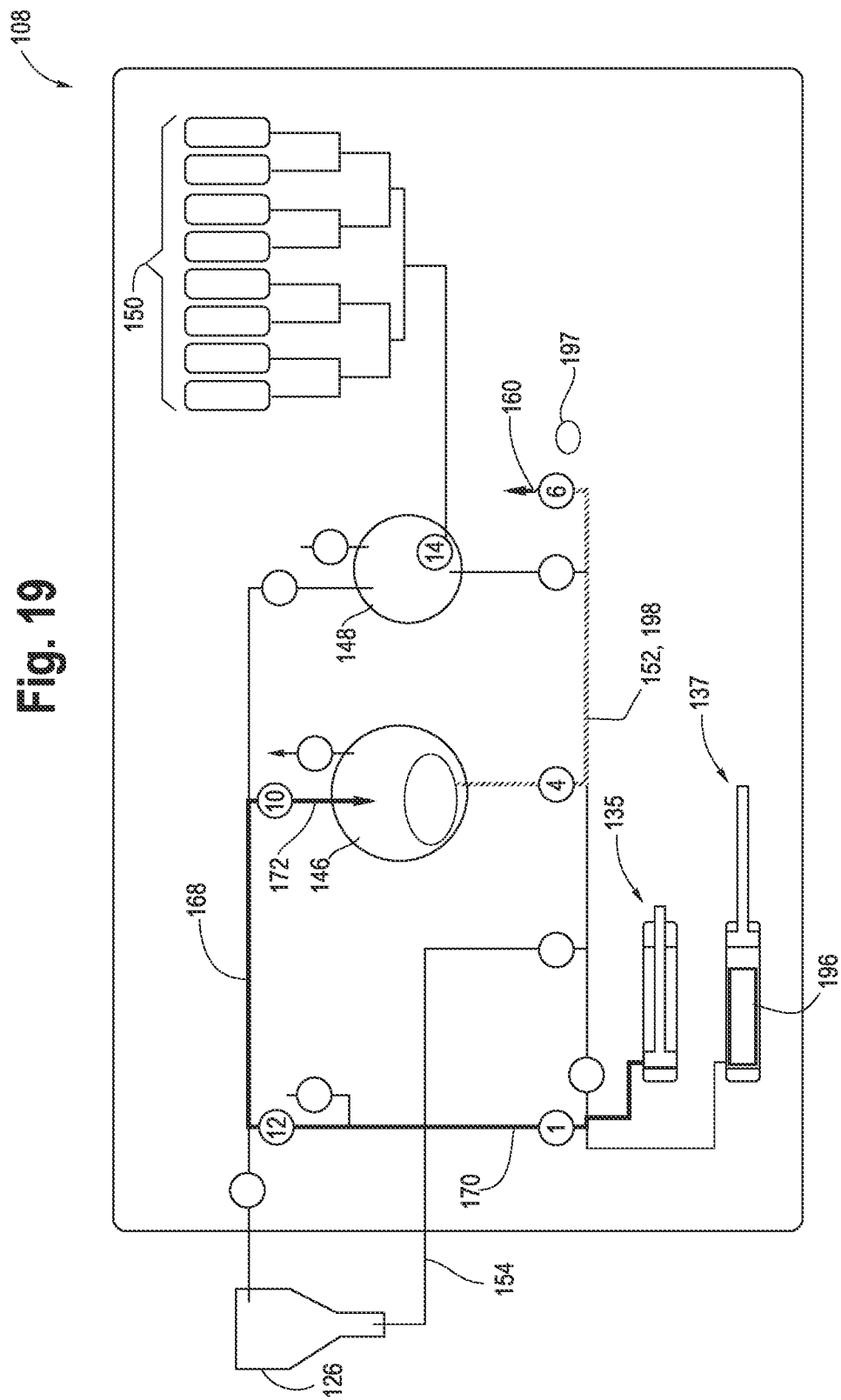

Referring to FIG. 18, the valves 3, 4, 9, 12, 13 close, the valve 11 opens, and the first pump 135 withdraws about 1 mL to about 5 mL (e.g., about 2 mL) of air from the waste reservoir 192 into the first pumping chamber 134 via the fluid channel 170 while the first amplification reaction takes place in the first reaction chamber 146, as shown in the color cyan. Referring to FIG. 19, the valve 11 closes, and the valves 12, 10, 4, 6 open. The first pump 135 drives the air contained in the first pumping chamber 134 into the first reaction chamber 146 via the fluid channels 170, 168, 172, thereby driving about 100 µL to about 400 µL (e.g., about 200 µL) of the first reaction product from the first reaction chamber 146 into a portion of the fluid channel 152 between the valves 4, 6 that defines a metering channel 198 over a period of about 5 s to about 10 s (e.g., about 7 s). An excess amount 197 of the first reaction product in the metering channel 198 flows into the terminal fluid channel 160, as shown in the color cyan.

Figure 20:
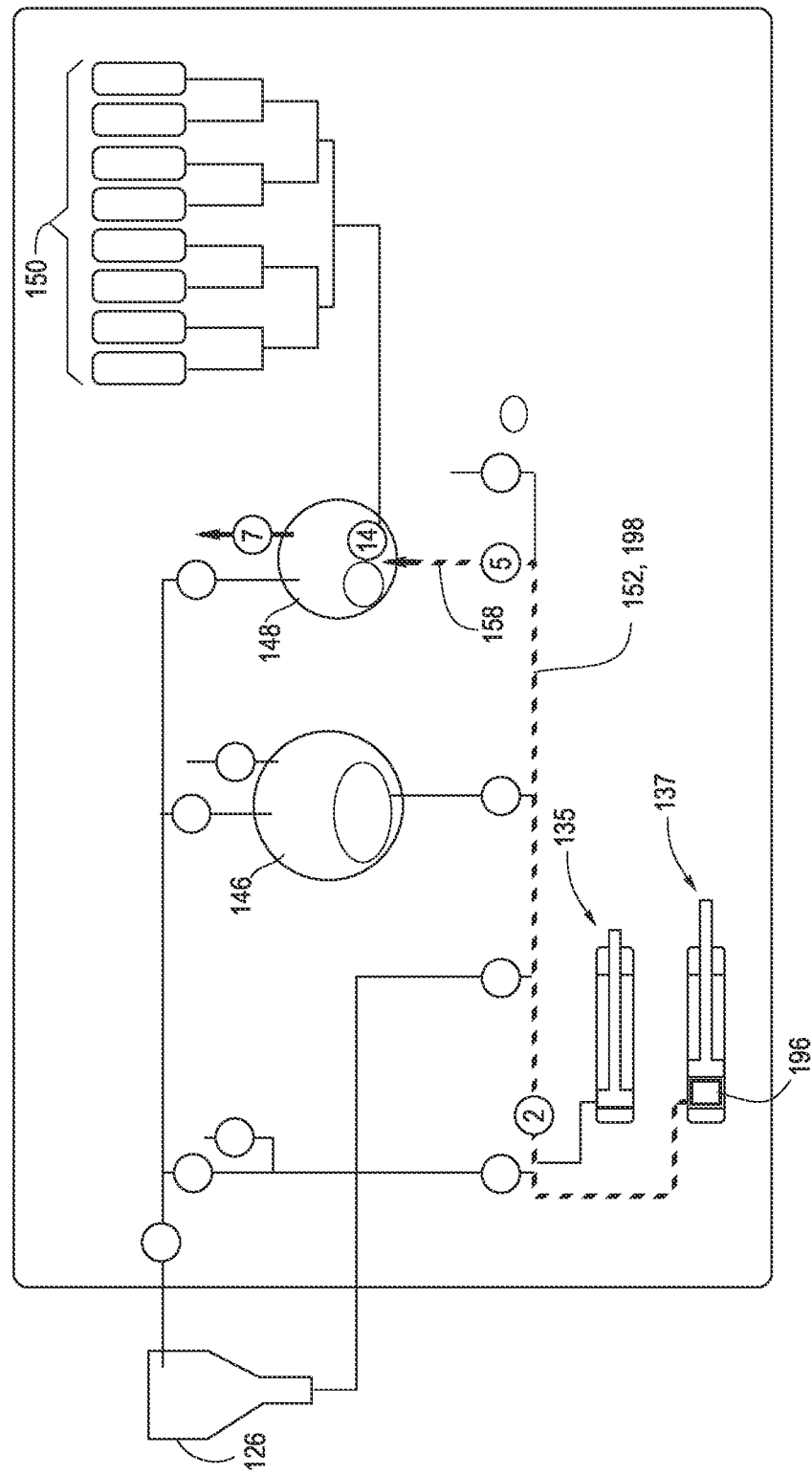

Referring to FIG. 20, the valves 1, 12, 10, 4, and 6 close, and the valves 5, 7 open. The second pump 137 drives about 200 µL to about 800 µL (e.g., about 400 µL) of the second liquid reagent 196 from the second pumping chamber 136 to the mixing chamber 146 via the metering channel 198 and the fluid channel 158, thereby also driving the first reaction product in the metering channel 198 into the mixing chamber 148 over a period of about 5 s to about 10 s (e.g., about 8 s). Within the metering channel 198 and the mixing chamber 148, the second liquid reagent 196 dilutes the first reaction product (e.g., at about 1:50) that was contained within the metering channel 198. A volume of about 500 µL to about 2000 µL (e.g., about 1000 µL) of the second liquid reagent 196 remains in the second pumping chamber 136. The mixing chamber 148 has a volume of about 5 µL to about 20 µL (e.g., about 8 µL) of the first reaction product, shown in yellow. The mixing chamber 148 is heated, and the second magnet 118 rotated to dissolve the pellet 123 in the first reaction product and the second liquid reagent 196, as shown in yellow. The mixing occurs for a period of about 2 s to about 10 s (e.g., about 5 s). Residual air in the mixing chamber 148 is vented to the waste reservoir 192 through the valve 7.

Figure 21:
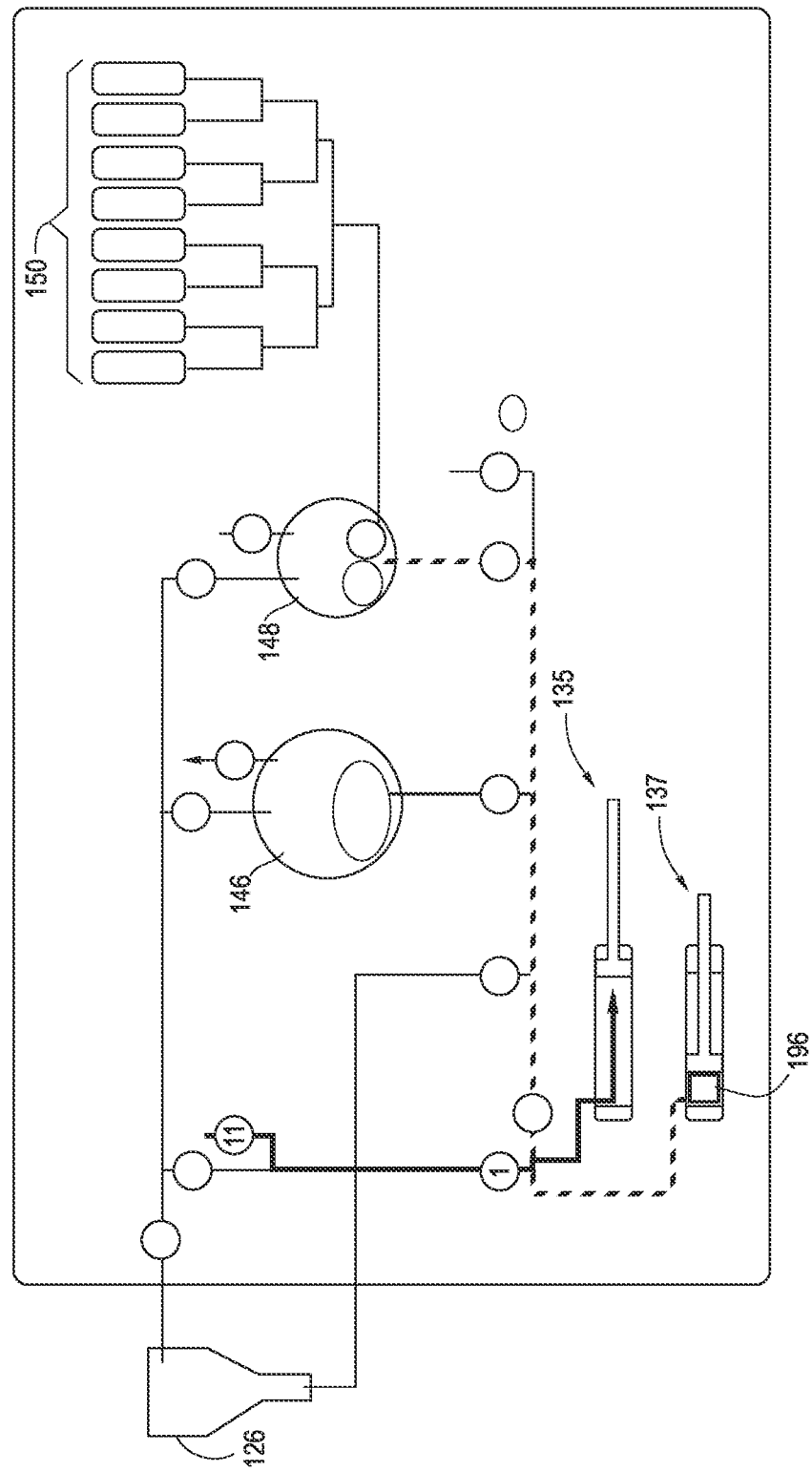
Figure 22:
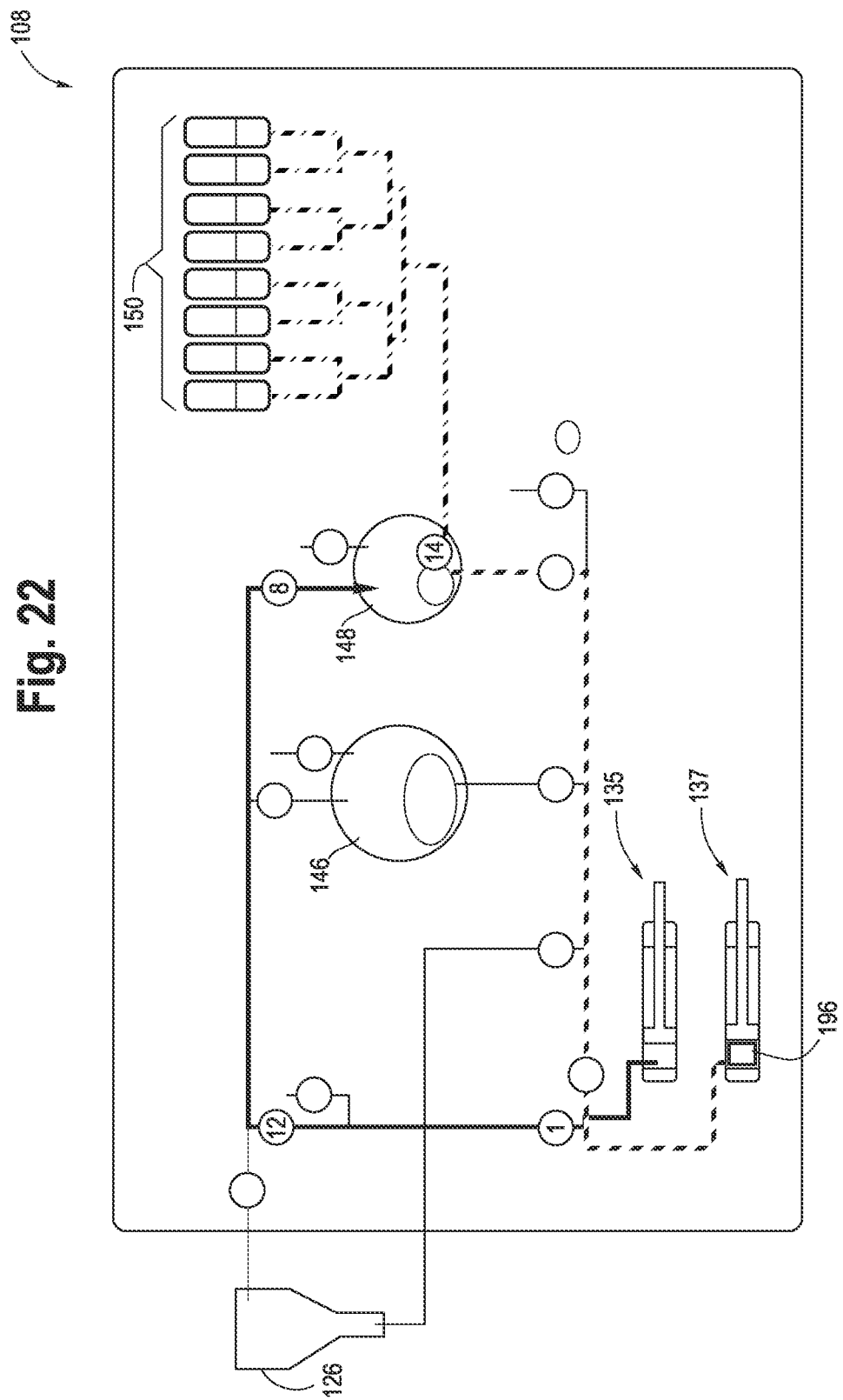

Referring to FIG. 21, the valves 5, 7 close, the valve 11 is opens, and the first pump 135 withdraws about 1000 µL to about 5000 µL (e.g., about 2000 µL) of air from the waste reservoir 192 into the first pumping chamber 134 via the fluid channel 170 while mixing occurs in the mixing chamber 148. Referring to FIG. 22, the valve 11 closes, and the valves 8, 12, 14 open. The first pump 135 drives about 200 µL to about 1000 µL (e.g., about 500 µL) of air from the first pumping chamber 134 to the mixing chamber via the fluid channels 170, 168, 176, thereby driving the first reaction product in the mixing chamber 146 into the second reaction chambers 150 via the fluid channel network 162 over a period of about 5 s to about 20 s (e.g., about 17 s). The first reaction product is driven against the air springs associated with the second reaction chambers 150 such that equal volumes of about 22.5 µL to about 27.5 µL (e.g., about 25.0 µL) of the first reaction product are delivered to the second reaction chambers 150, such that the second reaction chambers 150 are about 30% full.

A second amplification reaction occurs in the second reaction chambers 150 over a period of about 180 s to about 600 s (e.g., about 240 s), during which the second reaction chambers 150 are heated, and the third magnets 120 rotate or move vertically to dissolve the second reaction pellets 124 in the first reaction product. In some implementations, the second amplification reaction for amplifying the first amplified polynucleotide sequence is an RPA reaction, and the second reaction product includes a second amplified polynucleotide sequence that includes a smaller sequence completely contained within the first amplified polynucleotide sequence.

Figure 23:
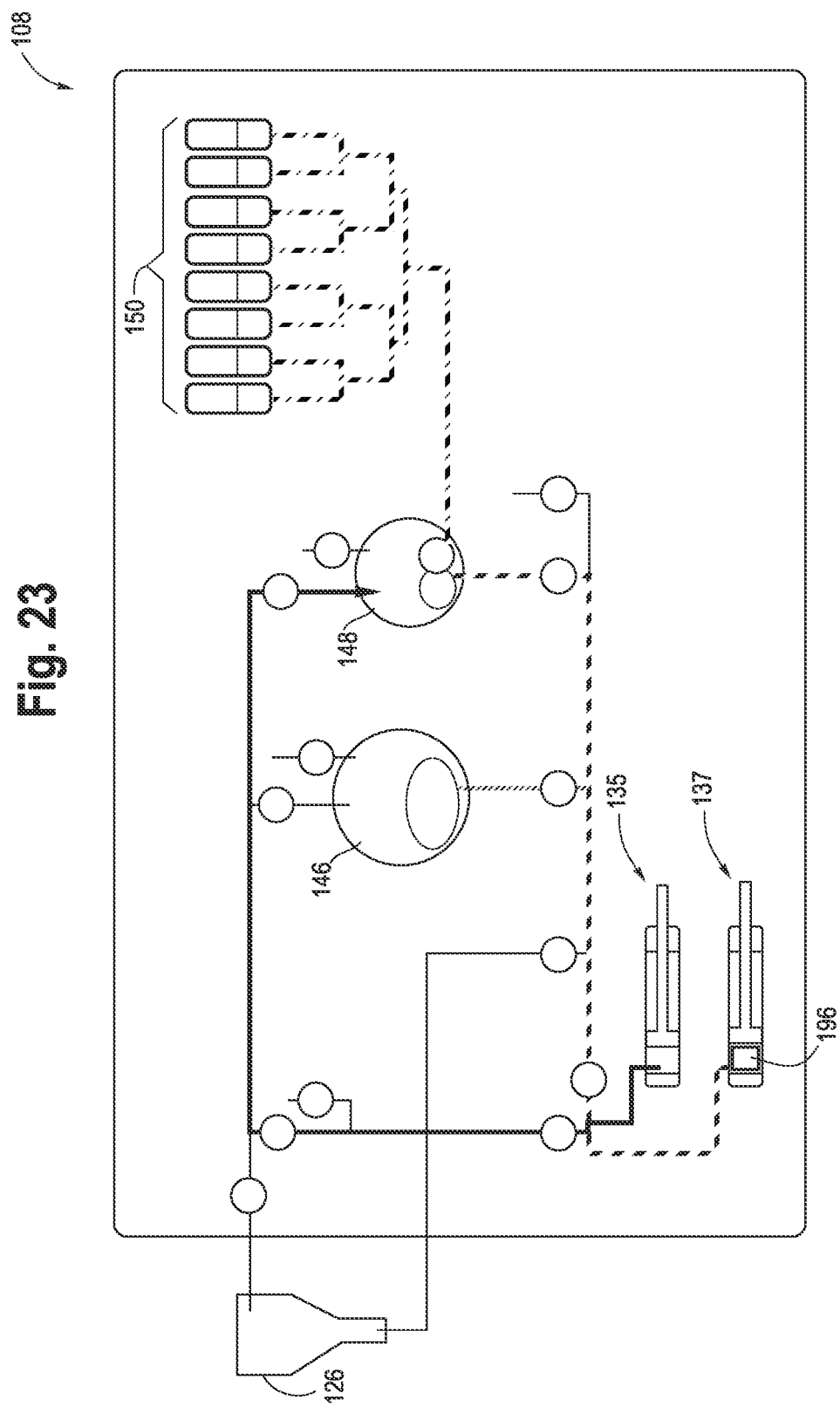

Referring to FIG. 23, the valves 1, 8, 14 close, and sequential fluorescence detection of the second amplification reaction is carried out. In some implementations, the sequential fluorescence detection includes labelling the second amplification product with a first oligonucleotide linked to a fluorophore and a quencher to yield a labelled second product, cleaving the quencher from the labelled second amplification product, and optically detecting a signal from the fluorophore (e.g., indicating the presence of the second amplification product). In some implementations, quencher is cleaved using a nuclease. In some implementations, the nuclease targets double-stranded DNA. In some implementations, the nuclease is formamidopyrimine-DNA glycosylase. The detection may be performed using the reader, which is adjacent the lid 106 and the cartridge 108 along the second reaction chambers 150 about every 5 s to about 20 s (e.g., about 15 s) over a period of about 3 min to about 10 min (e.g., about 4 min).

As measured from a time at which the sample is delivered to the sample chamber 126 to a time at which detection is completed, the assay may be performed within a period of less than about 30 min (e.g., less than about 15 min, less than about 10 min, or less than about 5 min) using the microfluidic device 100. Following detection, the microfluidic device 100 is ejected from the reader, and the microfluidic device 100 is removed manually from the reader. Owing at least in part to the closed system configuration of the microfluidic device 100 (e.g., following capping of the sample chamber 126), a risk of leakage contamination to the ambient environment is significantly reduced as compared to conventional devices used to carry out similar assays.

FIGS. 24-27 show additional exemplary embodiments and features of microfluidic devices described herein. Referring to FIG. 24, a device with exemplary dimensions is shown. In some embodiments, the device is approximately 82 mm by 106 mm by 11 mm in its broadest dimensions, although other dimensions are specifically contemplated (e.g., +/−5%, 10%, 15%, 20%, 30%, 40%, 50%, etc. Still referring to FIG. 24, in some embodiments, the device comprises an internal sloped portion 204 of the first reaction chamber 146. Still referring to FIG. 24, in some embodiments, the handle 206 of the device comprises full rounds on the grip edge for more ergonomic design.

Referring to FIG. 27, in some embodiments, the lid 106 of the device is attached to the device via snaps 207. In some embodiments, lid 106 lacks a V-notch 208, while the body of the device retains a V-notch 208 (shown in FIG. 24).

In some embodiments, valve configurations are arranged to minimize the size of the device (e.g., minimize the dimensions of the device). FIG. 24 shows exemplary valve configurations, although other arrangements are specifically contemplated. In some embodiments, shared welds between regions of fluid flow are avoided for ease of leak detection. For example, referring to FIG. 24, in some embodiments, region 150 has no shared welds between device components.

In some embodiments, robustness of the device is enhanced via molding techniques including, for example, thinner cored-out wall sections, strong cored-out features and robust core pins.

Figure 25A:
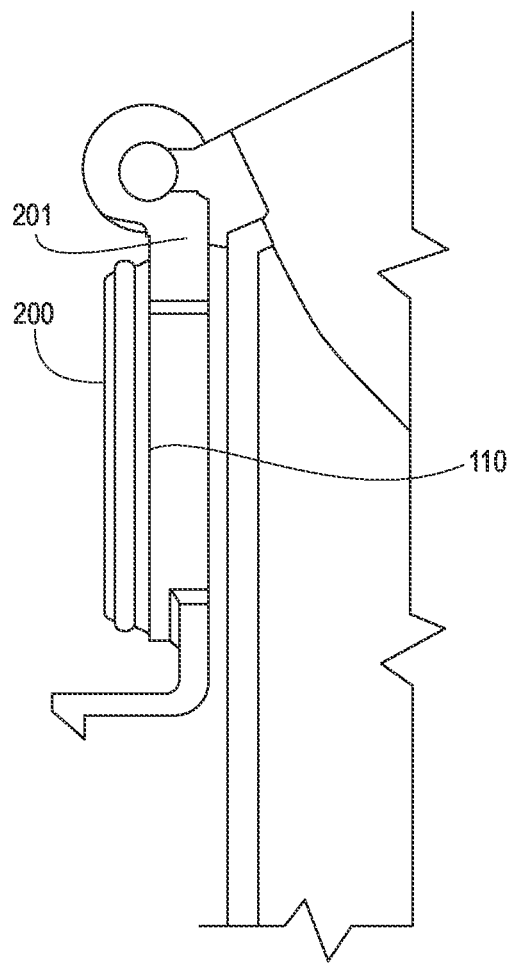
FIG. 25 shows exemplary cap design embodiments.
Figure 25B:
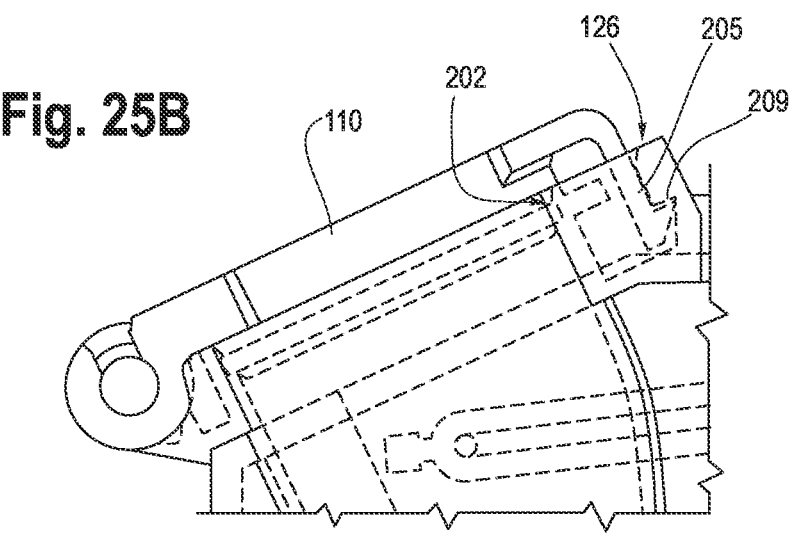
Figure 26:
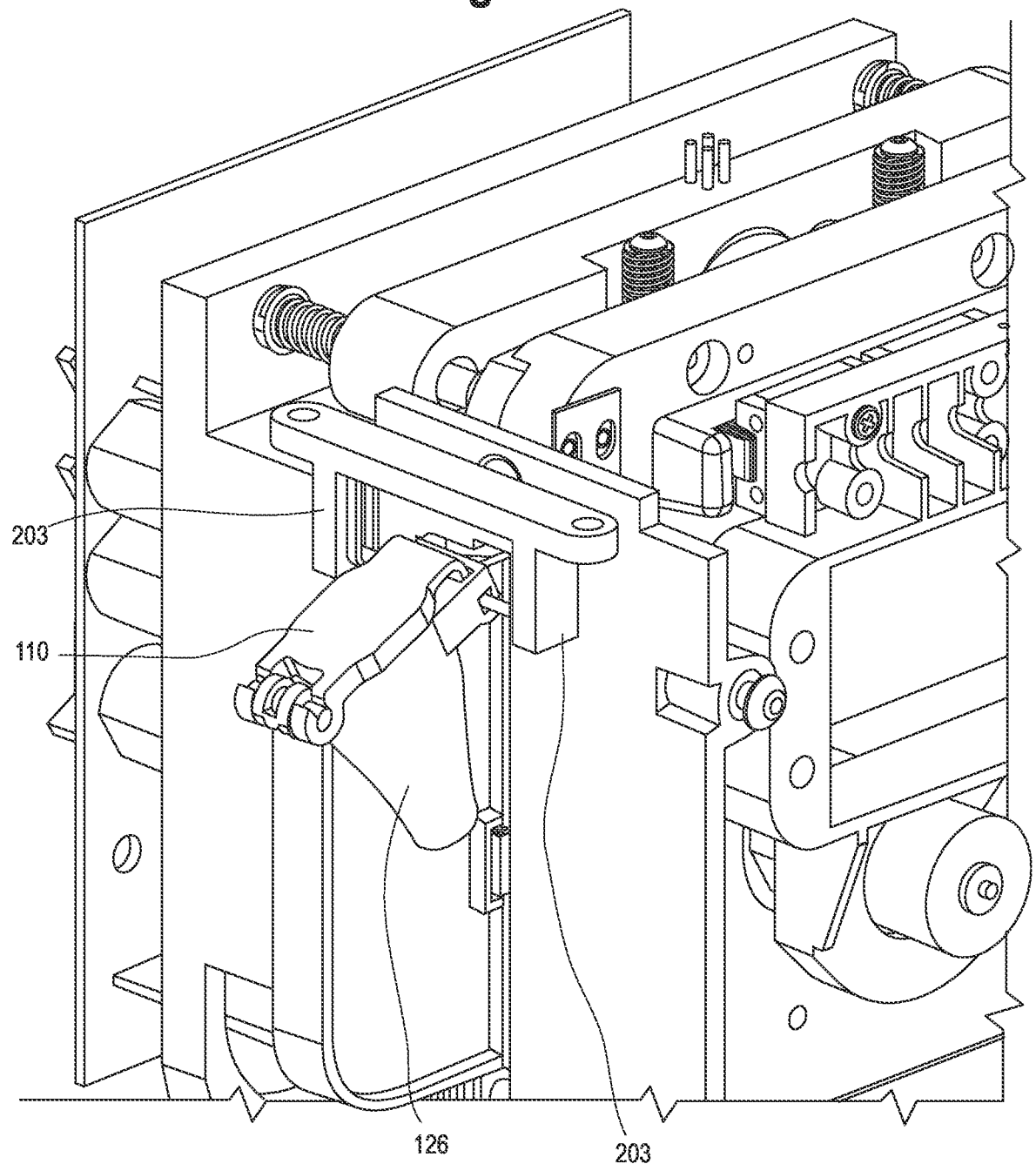
FIG. 26 shows exemplary cap closure detection components.

In some embodiments, the device comprises a leak-proof, sealed cap to minimize risk of and contamination by dangerous or hazardous material (e.g., biological samples comprising pathogens), including avoiding contamination of a detection instrument used with the devices. In some embodiments, this is accomplished with one or more or each of a sealed cap, cap closure sensors, and cap pressure sensors. FIGS. 25-26 show such exemplary embodiments.

Referring to FIG. 25, embodiments of cap 110 are shown. Referring to the upper panel of FIG. 25, detent feature 201, designed to secure cap 110 in an open position, is shown. Still referring to FIG. 25, cap gasket 200 is shown. Without being limited to a specific material, in some embodiments, cap gasket 200 is molded in place and comprises silicone. Still referring to FIG. 25, gasket seal rib 202 is shown. In some embodiments, the gasket and gasket seal rib prevent leaks of sample from sample chamber 106. Also referring to FIG. 25, a snap hook 205 component for sealing of the cap in the closed position is shown. The snap hook 205, in a closed position, interlocks with a mating structure 209 on an upper region of the sample chamber 126.

Referring to FIG. 26, cap position detection component 203 is shown. In some embodiments, cap position detection component 203 is configured to detect leaks and/or a cap that is not properly secured in place. In some embodiments, the cap position detection component is an optical cap closure sensor and/or a pressure detector.

In some embodiments, the cap position detection component 203 comprises an optical cap closure sensor. For example, in some embodiments, the cap closure detection component produces an optical beam across the cap opening that is broken when the cap 110 is secured in place (e.g., via snap hook 205 or other cap sealing component). In some embodiments, the device or an instrument that functions with the device is configured to cease operation or sound an alarm when the cap is not in the closed, sealed position (e.g., the optical beam is not broken).

In some embodiments, the cap position detection component 203 comprises a pressure sensor that measures the ability of the cap to resist pressure. In some embodiments, force feedback of pressure (e.g., provided by a pump of the device) is utilized to detect a cap that is not properly sealed or is exhibiting leaks. In some embodiments, pressures outside of the expected range (e.g., indicative of the cap not properly sealed or a cap that is leaking), results in an alarm or a ceasing of operations of the device or an instrument that functions with the device.

A number of embodiments of the invention have been described. Nevertheless, it will be understood that various modifications may be made without departing from the spirit and scope of the invention. Accordingly, other embodiments are within the scope of the claims following this detailed description.

For example, while the microfluidic device 100 has been described and illustrated as including eight second reaction chambers 150, in some embodiments, a microfluidic device that is substantially similar in construction and function to the microfluidic device 100 may include a different number of second reaction chambers, such as one, two, three, four, five, six, seven, or more than eight second reaction chambers.

While the elastomer layer 104, the cartridge 108, and the lid 106 have been described as having certain dimensions, in some embodiments, a microfluidic device that is substantially similar in construction and function to the microfluidic device 100 may include an elastomer layer, a cartridge, and a lid that have dimensions different from those indicated for the elastomer layer 104, the cartridge 108, and the lid 106.

While the cartridge 108 has been described and illustrated as including the optional intermediary pellet 123, in some embodiments, a microfluidic device that is similar in construction and function to the microfluidic device 100 may not include the optional intermediary pellet 123.

While the method illustrated by FIGS. 13-27 has been described with respect to certain time periods, fluid volumes, pellet constituencies, and liquid reagent constituencies that are applicable to certain assays, in some implementations, the microfluidic device 100 may be used to perform similar or different assays that involve different durations, fluid volumes, pellet constituencies, and liquid reagent constituencies.

While the devices and methods herein have been described as applications of Recombinase Polymerase Amplification (RPA) technology, other isothermal technologies for amplifying and detecting target nucleic acids may also be implemented in the microfluidic device 100 described herein (e.g., Nicking and Extension Amplification Reaction (NEAR) technology). Methods of RPA amplification and detection of RPA amplification products, as described herein, are described in detail in U.S. Pat. Nos. 7,399,590; 8,580,507; 7,270,981; 7,399,590; and 7,666,598; 7,435,561; US Patent Application Publication No. 2009/0029421; and International Patent Publication WO 2010/141940. NEAR methods are described in US Patent Application Publication Nos. 2009/0081670 and 2009/0017453 and U.S. Pat. Nos. 9,562,263 and 9,562,264. Each of the foregoing references is incorporated herein by reference in its entirety and considered part of the present disclosure.

What is claimed is:

1. A method comprising:
    providing a microfluidic device comprising: a first reaction chamber comprising a first magnet; and a second reaction chamber comprising a second magnet;
    mixing a sample fluid comprising a target nucleic acid with a first set of recombinase polymerase amplification (RPA) reagents;
    providing the sample fluid comprising the target nucleic acid and the RPA reagents to flail the microfluidic device, the target nucleic acid comprising a target polynucleotide sequence; and
    amplifying the target polynucleotide sequence under isothermal conditions, wherein the amplifying comprises:
        performing a first round of amplification on the target polynucleotide sequence in all the first reaction chamber to yield a first amplification product comprising a first amplified polynucleotide sequence;
        mixing a portion of the first amplification product with a second set of RPA reagents in flail the second reaction chamber; and
        performing a second round of amplification on the first amplified polynucleotide sequence in the second reaction chamber to yield a second amplification product comprising a second amplified polynucleotide sequence,
    wherein the second amplified polynucleotide sequence comprises a smaller sequence completely contained within the first amplified polynucleotide sequence produced during the first round of amplification,
    wherein the second amplification product is detected in less than approximately 30 minutes after providing the sample to the microfluidic device.

2. The method of claim 1, further comprising detecting said second amplification product.

3. The method of claim 2, wherein detecting said second amplification product comprises:
    labeling the second amplification product with a first oligonucleotide linked to a fluorophore and a quencher to yield a labeled second amplification product;
    cleaving the quencher from the labeled second amplification product; and
    detecting an optical signal from the fluorophore, wherein detecting the optical signal is indicative of the presence of the second amplification product.

4. The method of claim 3, wherein cleaving the quencher comprises cleaving the quencher using a nuclease.

5. The method of claim 4, wherein the nuclease cleaves double-stranded DNA.

6. The method of claim 4, wherein the nuclease is a formamidopyrimine-DNA glycosylase.

7. The method of claim 1, wherein the sample fluid is or is prepared from blood, sputum, mucus, saliva, tears, or urine.

8. The method of claim 1, wherein the method further comprises obtaining a sample from an animal.

9. The method of claim 8, wherein the method further comprises obtaining a sample from a human.

10. The method of claim 1, wherein the target nucleic acid is a nucleic acid from an animal pathogen.

11. The method of claim 10, wherein the animal pathogen is a bacterium, a single-stranded DNA virus, a double-stranded DNA virus, or a single-stranded RNA virus.

12. The method of claim 1, wherein the target nucleic acid is a double-stranded DNA, a single-stranded DNA, or an RNA.

13. The method of claim 1, wherein the target nucleic acid is a genomic DNA, a plasmid DNA, a viral DNA, a viral RNA, a mitochondrial DNA, a cDNA, a synthetic double-stranded DNA, or a synthetic single-stranded DNA.

14. The method of claim 10, wherein the animal pathogen is an influenza A virus, an influenza B virus, or a Respiratory Syncytial Virus (RSV).

15. The method of claim 1, wherein the target nucleic acid comprises two target polynucleotide sequences or three target polynucleotide sequences.

16. The method of claim 1, wherein the second amplification product is detected in real time.

17. The method of claim 1, wherein the method further comprises lysing the sample prior to amplification.

18. The method of claim 1, wherein the second amplification product is detected in less than approximately 15 minutes after providing the sample to the microfluidic device.

* * * * *

UNITED STATES PATENT AND TRADEMARK OFFICE
CERTIFICATE OF CORRECTION

| | | |
|---|---|---|
| PATENT NO. | : 11,872,554 B2 | |
| APPLICATION NO. | : 16/812961 | |
| DATED | : January 16, 2024 | |
| INVENTOR(S) | : Alexander Schenk zu Schweinsberg et al. | |

It is certified that error appears in the above-identified patent and that said Letters Patent is hereby corrected as shown below:

In the Claims

Claim 1, Column 17, Line 23 reads:
"acid and the RPA reagents to flail the microfluidic"

Whereas it should read:
"acid and the RPA reagents to the microfluidic"

And

Claim 1, Column 17, Line 29 reads:
"polynucleotide sequence in all the first reaction"

Whereas it should read:
"polynucleotide sequence in the first reaction"

And

Claim 1, Column 17, Line 33 reads:
"a second set of RPA reagents in flail the second"

Whereas it should read:
"a second set of RPA reagents in the second"

Signed and Sealed this
Twenty-sixth Day of March, 2024

Katherine Kelly Vidal
*Director of the United States Patent and Trademark Office*